US007482360B2

(12) United States Patent
Burnett et al.

(10) Patent No.: US 7,482,360 B2
(45) Date of Patent: Jan. 27, 2009

(54) FUSED TETRACYCLIC MGLUR1 ANTAGONISTS AS THERAPEUTIC AGENTS

(75) Inventors: Duane A. Burnett, Bernardsville, NJ (US); Wen-Lian Wu, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/524,867

(22) Filed: Sep. 21, 2006

(65) Prior Publication Data
US 2008/0312218 A1    Dec. 18, 2008

Related U.S. Application Data

(60) Provisional application No. 60/720,028, filed on Sep. 23, 2005.

(51) Int. Cl.
*A01N 43/42* (2006.01)
*A61K 31/44* (2006.01)
*C07D 487/00* (2006.01)
*C07D 471/00* (2006.01)
*C07D 239/00* (2006.01)
*C07D 491/00* (2006.01)

(52) U.S. Cl. .................. 514/285; 514/287; 544/247
(58) Field of Classification Search .......... 514/285, 514/287; 544/247
See application file for complete search history.

(56) References Cited

U.S. PATENT DOCUMENTS

| 5,783,575 A | 7/1998 | Jakobsen et al. |
| 2006/0167029 A1* | 7/2006 | Matasi et al. ............... 514/267 |

FOREIGN PATENT DOCUMENTS

| EP | 0 512 817 A1 | 11/1992 |
| WO | WO 97/05137 A1 | 2/1997 |
| WO | WO 02/062803 A1 | 8/2002 |
| WO | WO 2006/081072 A1 | 3/2006 |
| WO | WO 2006/002051 A1 | 5/2006 |
| WO | WO 2006/058724 | * 6/2006 |
| WO | WO 2006/058724 A1 | 8/2006 |

OTHER PUBLICATIONS

West, Anthony R., Solid State Chemistry and Its Applications, Wiley, New York, 1988, 358.*
Pellicciari R, et al., Synthesis and pharmacological characterization of all sixteen stereoisomers of 2-(2'-carboxy-3'-phenylcyclopropyl)glycine. Focus on (2S,1'S,2'S,3'R)-2-(2'-carboxy-3'-phenylcyclopropyl)glycine, a novel and selective group II metabotropic glutamate receptors antagonist. J. of Med. Chem. (1996) vol. 39, No. 11, pp. 2259-69.*
Bhave et al., "Peripheral group I metabotropic glutamate receptors modulate nociception in mice", Nature Neuroscience, (2001) vol. 4, pp. 417-423.

Bousquet E. et al., Synthesis and Pharmacological Activity of 3-Substituted Pyrido(3', 2':4,5) Thieno(3,2-d)Pyrimidin-4(3H)-Ones, Farmaco, Edizione Scientifica, Societa Chimica Italiana, Pavia, IT, (1984) vol. 39, No 2, pp. 110-119.
Dolan et al., "Behavioral evidence supporting a differential role for spinal group I and II metabotropic glutamate receptors in inflammatory hyperalgesia in sheep", Neuropharmacology, (2002) vol. 43, pp. 319-326.
Dolan et al., "Up-regulation of metabotropic glutamate receptor subtypes 3 and 5 in spinal cord in a clinical model of persistent inflammation and hyperalgesia", Pain, (2003), vol. 106, pp. 501-512.
Fisher et al., "Hyperalgesia and allodynia induced by intrathecal (RS)-dihydroxyphenylglycine in rats", NeuroReport, (1998) vol. 9, pp. 1169-1172.
Fundytus et al., "Antisense oligonucleotide knockdown of mGluR$_1$ alleviates hyperalgesia and allodynia associated with chronic inflammation", Pharmacology, Biochemistry and Behavior, (2002) vol. 73, pp. 401-140.
Fundytus et al., "In vivo antinociceptive activity of anti-rate mGluR$_1$ and mGluR$_5$ antibodies in rats", NeuroReport, (1998) vol. 9, pp. 731-735.

(Continued)

*Primary Examiner*—James O. Wilson
*Assistant Examiner*—Erich A Leeser
(74) *Attorney, Agent, or Firm*—Keith D. MacMillan; William Y. Lee

(57) ABSTRACT

In its many embodiments, the present invention provides tetracyclic compounds of formula I or formula II (wherein the various moieties are as defined herein) useful as metabotropic glutamate receptor (mGluR) antagonists, particularly as selective metabotropic glutamate receptor 1 antagonists, pharmaceutical compositions containing the compounds, and methods of treatment using the compounds and compositions to treat diseases associated with metabotropic glutamate receptor (e.g., mGluR1) such as, for example, pain, migraine, anxiety, urinary incontinence and neurodegenerative diseases such Alzheimers disease.

formula I

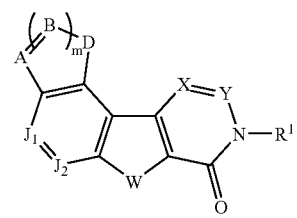

formula II

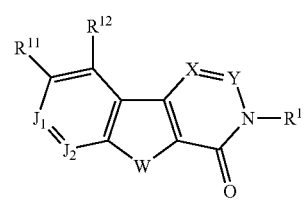

23 Claims, No Drawings

OTHER PUBLICATIONS

Fundytus et al., "Knockdown of spinal metabotropic glutamate receptor 1 (mGluR₁) alleviates pain and restores opioid efficacy after nerve injury in rats", British Journal of Pharmacology, (2001) vol. 132, pp. 354-367.

Mills and Hulsebosch, "Increased expression of metabotropic glutamate receptor subtype 1 on spinothalamic neurons following spinal cord injury in the rat", Neuroscience Letters (2002) vol. 319, pp. 59-62.

Neugebauer et al., "Peripheral metabotropic glutamate receptors: fight the pain where it hurts", Trends in Neurosciences, (2001) vol. 24, pp. 550-552.

Neugebauer et al., "Role of Metabotropic Glutamate Receptor Subtype mGluR1 in Brief Nociception and Central Sensitization of Primate STT Cells", Journal of Neurophysiology, (1999) vol. 82, pp. 272-282.

Tacconi G et al., "Indolizzazione di 3-piridilidrazoni della 2,3-dichetopiperidina", Annali Di Chimica, Societa Chimica Italiana, Rome, IT, (1965) vol. 55, No. 12, pp. 1223-1232.

Young et al., "Antisense Ablation of Type I Metabotropic Glutamate Receptor mGluR₁ Inhibits Spinal Nociceptive Transmission", The Journal of Neuroscience, (1998) vol. 18, pp. 10180-10188.

Young et al., "Behavioural and electrophysiological evidence supporting a role for group I metabotropic glutamate receptors in the mediation of nociceptive inputs to the rat spinal cord", (1997) vol. 777, pp. 161-169.

Young et al., "Evidence for a Role of Metabotropic Glutamate Receptors in Sustained Nociceptive Inputs to Rat Dorsal Horn Neurons", Neuropharmacology, (1994), vol. 33, pp. 141-144.

Zheng G.Z. et al., "Structure—Activity Relationship of Triazafluorenone Derivatives as Potent and Selective mGluR1 Antagonists", Journal of Medicinal Chemistry, American Chemical Society, Washington, US, (2005) vol. 48, No. 48, pp. 7374-7388.

Chemical Abstracts Service, Columbus, Ohio; Mar. 2, 2005—XP002428679; Database accession No. 840457-75-2; abstract; compounds 840457-75-2.

Chemical Abstracts Service, Columbus, Ohio; Feb. 24, 2005—XP002428680; Database accession No. 836632-30-5; abstract; compounds 836632-30-5.

Chemical Abstracts Service, Columbus, Ohio; Dec. 20, 2004—XP002428681; Database accession No. 799818-75-0; abstract; compounds 799818-75-0.

Chemical Abstracts Service, Columbus, Ohio; Dec. 20, 2004—XP002428682; Database accession No. 799809-04-4; abstract; compounds 799809-04-4.

Chemical Abstracts Service, Columbus, Ohio; Dec. 20, 2004—XP002428683; Database accession No. 799778-39-5; abstract; compounds 799778-39-5.

Chemical Abstracts Service, Columbus, Ohio; Jun. 21, 2004—XP002428684; Database accession No. 696658-55-6; abstract; compounds 696658-55-6.

Chemical Abstracts Service, Columbus, Ohio; Apr. 12, 2004—XP002428685; Database accession No. 674332-81-1; abstract; compounds 674332-81-1.

Chemical Abstracts Service, Columbus, Ohio; Apr. 9, 2004—XP002428686; Database accession No. 673495-74-4; abstract; compounds 673495-74-4.

Chemical Abstracts Service, Columbus, Ohio; Apr. 9, 2004—XP002428687; Database accession No. 673493-15-7; abstract; compounds 673493-15-7.

Chemical Abstracts Service, Columbus, Ohio; Apr. 9, 2004—XP002428688; Database accession No. 673489-94-6; abstract; compounds 673489-94-6.

Chemical Abstracts Service, Columbus, Ohio; Apr. 8, 2004—XP002428689; Database accession No. 672920-18-2; abstract; compounds 672920-18-2.

Chemical Abstracts Service, Columbus, Ohio; Apr. 7, 2004—XP002428690; Database accession No. 672281-18-4; abstract; compounds 672281-18-4.

Chemical Abstracts Service, Columbus, Ohio; Apr. 7, 2004—XP002428691; Database accession No. 672264-77-6; abstract; compounds 672264-77-6.

Chemical Abstracts Service, Columbus, Ohio; Mar. 23, 2003—XP002428692; Database accession No. 500276-33-5; abstract; compounds 500276-33-5.

Chemical Abstracts Service, Columbus, Ohio; Mar. 3, 2003—XP002428693; Database accession No. 496771-54-1; abstract; compounds 496771-54-1.

Chemical Abstracts Service, Columbus, Ohio; Feb. 12, 2003—XP002428694; Database accession No. 488801-73-6; abstract; compounds 488801-73-6.

Chemical Abstracts Service, Columbus, Ohio; Feb. 11, 2003—XP002428695; Database accession No. 488723-48-4; abstract; compounds 488723-48-4.

Chemical Abstracts Service, Columbus, Ohio; Nov. 20, 2001—XP002428696; Database accession No. 371134-99-5; abstract; compounds 371134-99-5.

International Search Report for International Application No. PCT/US2005/020972, mailed Oct. 26, 2005 (5 pages) for CN06202.

International Search Report for International Application No. PCT/US2006/046943, mailed Aug. 30, 2007 (5 pages) for CN06202-01.

International Search Report for International Application No. PCT/US2006/031972, mailed Jan. 16, 2007 (4 pages) for CN06342.

International Search Report for International Application No. PCT/US2006/031944, mailed Feb. 13, 2007 (5 pages) for CN06343.

International Search Report for International Application No. PCT/US2006/036858, mailed Apr. 24, 2007 (6 pages) for CN06344.

Attachment "A" U.S. Appl. No. 11/152,535, filed Jun. 14, 2005 (Julius J. Matasi), 2 pages.

Attachment "B" U.S. Appl. No. 11/152;535, 1 page from Examiner, p. 1 of 1.

Attachment "C" U.S. Appl. No. 11/301,672; filed Dec. 13, 2005 (Julius J. Matasi et al), 2 pages.

Attachment "D" U.S. Appl. No. 11/505,140, filed Aug. 16, 2006 (Chad E. Bennett, et al.), 3 pages.

* cited by examiner

FUSED TETRACYCLIC MGLUR1 ANTAGONISTS AS THERAPEUTIC AGENTS

This application claims the benefit of U.S. Provisional Application Ser. No. 60/720,028, filed Sep. 23, 2005, which is incorporated herein by reference in its entirety.

FIELD OF THE INVENTION

The present invention relates to fused tetracyclic compounds useful as metabotropic glutamate receptor (mGluR) antagonists, particularly as selective metabotropic glutamate receptor 1 antagonists, pharmaceutical compositions containing the compounds, and methods of treatment using the compounds and compositions to treat diseases associated with metabotropic glutamate receptors (e.g., mGluR1) such as, for example, pain, migraine, anxiety, urinary incontinence and neurodegenerative diseases such as Alzheimer's disease.

BACKGROUND OF THE INVENTION

Glutamate is an important excitatory neurotransmitter in the mammalian central nervous system. Glutamate synaptic responses in the central nervous system (CNS) are mediated via activation of two families of receptors: ligand-gated cation channels, referred to as ionotropic glutamate receptors, and G-protein-coupled receptors known as metabotropic glutamate receptors (mGluRs). Thus far, eight mGluR subtypes, together with splice variants, have been cloned and characterized in functional studies (Schoepp et al. *Neuropharmacology*, 1999, 38, 1431-1476). The eight mGluRs are grouped into three classes based on structural homology, pharmacology, and signal transduction mechanisms.

Group I receptors (mGluR1 and mGluR5) couple through $G_{q/11}$ proteins to the activation of phospholipase C (PLC) resulting in phosphoinositide (PI) hydrolysis, the release of calcium from intracellular stores. While group II (mGluR2 and mGluR3) and III (mGluR4, mGluR6 mGluR7 and mGluR8) are negatively coupled to adenyl cyclase (AC) through $G_i/G_o$ proteins thereby inhibiting cyclic AMP (cAMP) formation (A. Francesconi and R. M. Duvoisin, *J. Biol. Chem.* 1998, 273(10), 5615-5624).

Glutamate and Pain

Chronic pain is an area of high unmet medical need. Current therapies are not adequate and chronic pain is often refractory to most commonly used analgesics, including opioids. Glutamate plays a major role in nociceptive processing. Glutamate receptors, including mGluRs, are expressed in relevant areas of the brain, spinal cord and periphery that are involved in pain sensation and transmission.

Chronic pain may be due to tissue injury and diseases (inflammatory pain) or to the central and peripheral nervous system (neuropathic pain) and is associated with severe chronic sensory disturbances characterized by spontaneous pain, hyperalgesia (exaggerated responsiveness to painful stimuli) and allodynia (wrong perception of non-noxious stimuli as painful). Prevalent symptoms in human patients include cold hyperalgesia, mechanical allodynia and less commonly, heat hyperalgesia.

Chronic pain is a true disease. It is believed to be a result of the plasticity at synapses in nociceptive processing centers, a phenomenon referred to as "central sensitization" which consists of increased excitability of spinal cord dorsal horn neurons. Glutamate receptors have been identified for their key role in central sensitization. Plasticity at synapses involved in nociceptive processing requires activation of ionotropic glutamate receptors such as NMDA and this plasticity is modulated by mGluRs including mGluR1. NMDA receptor antagonists have been tested in experimental therapies for the prevention and treatment of persistent pain following injury. However, there are significant undesiderable side effects associated with the use of NMDA antagonists due largely to the critical role of those receptors in normal excitatory synaptic transmission throughout the nervous system. These side effects include pyschosis, hyperactivity, fatigue, dizziness, and in the case of higher levels of NMDA antagonists, amnesia and neuronal toxicity. Drugs designed to antagonize mGluR1 receptors are expected to have less side effect liability since they appear to selectively modulate the pathologically abnormal spinal NMDA receptor activation associated with persistent pain states whilst having little effect on the normal spinal synaptic processes involved in non-painful sensory perception. Thus, mGluR antagonists might perform well clinically in chronic pain states because they avoid the side effects inherent to widespread spinal and supraspinal NMDA receptor antagonism.

mGluR1 and Pain

A number of behavioral (Fisher et al. *Neuroreport*, 1998, 20, 1169-1172; Fundytus et al. *Neuroreport*, 1998, 9, 731-735; Bhave et al. *Nature Neurosci.*, 2001, 4, 417-423; Dolan et al. *Neuropharmacology*, 2002, 43, 319-326; Dolan et al. *Pain*, 2003, 106, 501-512) and electrophysiological (Young et al. *Neuropharmacology*, 1994, 33, 141-144; and Young et al. *Brain Res.*, 1997, 777, 161-169) studies have demonstrated a specific role for Group I mGluRs, and in particular mGluR1 receptors, in nociceptive processing in the CNS, including mechanisms of hyperalgesia and inflammation. In the spinal cord, mGluR1 appears to be localized primarily on postsynaptic elements throughout the dorsal and ventral horns. (Neugebauer, *Trends Neurosci.*, 2001, 24, 550-552). The intrinsic activation of spinal mGluR1 in chronic nociception has been demonstrated using antagonists, antibodies and antisense oligonucleotides. Intrathecal administration of an mGluR1 antagonist produced antinociceptive effects in the second phase of formalin-induced nociceptive behavior (Neugebauer, *Trends Neurosci.*, 2001, 24, 550-552). Behavioral studies have also addressed the role of spinal mGluR1 receptors in the spinal injury and ligation models of neuropathic pain. Expression of mGluR1 is increased in rats following spinal cord injury and this may mediate the chronic central pain induced by the injury (Mills and Hulsebosch, *Neurosci. Lett.*, 2002, 319, 59-62). Knockdown of spinal mGluR1 by intrathecal infusion of antisense oligonucleotides attenuated cold hyperalgesia and mechanical allodynia in neuropathic rats (Fundytus et al. *Br. J. Pharmacol.*, 2001, 132, 354-367; and Fundytus et al. *Pharmacol. Biochem. Behav.*, 2002, 73, 401-410). Additionally, spinal administration of anti-mGluR1 IgG antibodies reduced cold hyperalgesia, but not mechanical allodynia, in neuropathic rats (Fundytus et al. *Neuroreport*, 1998, 9, 731-735). The critical role of spinal mGluR1 receptors in pain-related central sensitization is emphasized at the single cell level by electrophysiological in vivo studies in anesthetized animals. Intraspinal administration of an mGluR1 antagonist inhibited the responses of primate spinothalamic tract neurons to brief noxious, but not innocuous, mechanical cutaneous stimuli, as well as central sensitization in the capsaicin pain model (Neugebauer et al. *J. Neurophysiol.*, 1999, 82, 272-282). In rats with knocked down mGluR1 expression, the responses of multireceptive dorsal horn neurons to noxious input evoked by repeated topical applications of the C-fiber irritant mustard oil were significantly reduced compared to control neurons; the

SUMMARY OF THE INVENTION

In its many embodiments, the present invention provides a novel class of tetracyclic compounds useful as metabotropic glutamate receptor (mGluR) antagonists, particularly as selective mGluR1 antagonists, pharmaceutical compositions comprising one or more such compounds, methods of preparing pharmaceutical formulations comprising one or more such compounds, and methods of treatment, prevention, inhibition or amelioration of one or more diseases associated with the mGluRs, particularly mGluR1, using such compounds or pharmaceutical compositions.

In one aspect, the present application discloses a compound of formula I:

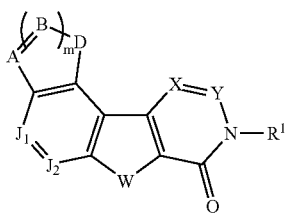

formula I or a pharmaceutically acceptable salt or solvate thereof, wherein:

W is S, O, or $N(R^{10})$;

X is N or CR3;

Y is N or $CR^2$;

$J_1$ and $J_2$ are each independently $C(R^4)$ or N;

$R^1$ is selected from the group consisting of —H, —$NR^5R^6$, —$OR^5$, —$SR^9$, —CN, —$C(O)R^6$, —$C(O_2)R^6$, —$OC(O)R^6$, —$C(O)NR^6R^7$, —$N(R^6)C(O)R^7$, —$S(O_2)NR^6R^7$—$N(R^6)S(O_2)R^9$, —$N(R^6)C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^2$ and $R^3$ are each independently selected from the group consisting of H, halo, —CN, —$NO_2$, —$OR^5$, —$SR^9$, —$NR^5R^6$, —$C(O)R^6$, —$C(O_2)R^6$, —$OC(O)R^6$, —$C(O)NR^6R^7$, —$N(R^6)C(O)R^7$, —$OS(O_2)R^9$, —$S(O_2)R^9$, —$S(O_2)NR^6R^7$, —$N(R^6)S(O_2)R^9$, and —$N(R^6)C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^4$ is independently selected from the group consisting of H, halo, —CN, —$NHC(O)R^6$, —$NHSO_2R^9$, —$NR^5R^6$, —$OR^5$, —$C(O)R^6$, —$C(O_2)R^6$, —$C(O)NR^6R^7$; and alkyl, alkoxy, alkenyl, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^5$ is selected from the group consisting of H, —$C(O)OR^6$, —$SO_2R^9$, —$C(O)NR^6R^7$, and alkyl, cycloalkyl, aryl, arylalkyl, heteroaryl, heteroarylalkyl, heterocyclyl, and heterocyclylalkyl groups optionally substituted with at least one $R^8$;

$R^6$ and $R^7$ are independently selected from the group consisting of H and alkyl, cycloalkyl, aryl, arylalkyl, heteroaryl, heteroarylalkyl, heterocyclyl, and heterocyclylalkyl groups optionally substituted with at least one $R^8$; or $R^5$ and $R^6$ or $R^6$ and $R^7$, when attached to the same nitrogen atom, optionally taken together with the nitrogen atom form a 3-8 membered heterocyclic ring containing 0-3 heteroatoms independently selected from O, N or S in addition to said nitrogen atom;

$R^8$ is selected from the group consisting of H, halo, —$OR^5$, —$NO_2$, —CN, —$NR^6C(O)R^7$, —$NR^6SO_2R^9$, —$NR^5R^6$, —$C(O)R^6$, —$C(O)OR^6$, —$C(O)NR^6R^7$, —$S(O_2)NR^6R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one of halo, —CN, —$NO_2$, —$OR^5$, —$SR^9$, —$NR^6R^7$, —$C(O)R^6$, —$C(O_2)R^6$, —$OC(O)R^6$, —$C(O)NR^6R^7$, —$N(R^6)C(O)R^7$, —$OS(O_2)R^9$, —$S(O_2)R^9$, —$S(O_2)NR^6R^7$, —$N(R^6)C(O)NR^6R^7$, and —$NR^6SO_2R^9$;

$R^9$ is selected from the group consisting of alkyl, cycloalkyl, aryl, arylalkyl, heteroaryl, heteroarylalkyl, heterocyclyl, and heterocyclylalkyl groups optionally substituted with at least one $R^8$;

$R^{10}$ is selected from the group consisting of H, —$C(O)R^6$, —$C(O)OR^6$, —$SO_2R^9$, —$C(O)NR^6R^7$, and alkyl, cycloalkyl, aryl, arylalkyl, heteroaryl, heteroarylalkyl, heterocyclyl, and heterocyclylalkyl groups optionally substituted with at least one $R^8$, A is selected from the group consisting of $CHR^4$, $CR^4$, O, S, N, $NR^4$, C=O, and C=S;

B is selected from the group consisting of N, $NR^4$, $CHR^4$, $CR^4$, O, S, C=O, C=S, and C—S—$R^9$;

D is selected from the group consisting of $CHR^4$, O, S, and $NR^4$; and m is 1-3.

In another aspect, the present application discloses a compound of formula I or a pharmaceutically acceptable salt or solvate thereof, wherein:

W is S, O, or $N(R^{10})$;

X is N or $CR^3$;

Y is N or $CR^2$;

$J_1$ and $J_2$ are each independently $C(R^4)$ or N;

$R^1$ is selected from the group consisting of —H, —$NR^5R^6$, —$R^5$, —$SR^9$, —CN, —$C(O)R^6$, —$C(O_2)R^6$, —$OC(O)R^6$, —$C(O)NR^6R^7$, —$N(R^6)C(O)R^7$, —$S(O_2)NR^6R^7$—$N(R^6)S(O_2)R^9$, —$N(R^6)C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^2$ and $R^3$ are each independently selected from the group consisting of H, halo, —CN, —$NO_2$, —$OR^5$, —$SR^9$, —$NR^5R^6$, —$C(O)R^6$, —$C(O_2)R^6$, —$OC(O)R^6$, —$C(O)NR^6R^7$, —$N(R^6)C(O)R^7$, —$OS(O_2)R^9$, —$S(O_2)R^9$, —$S(O_2)NR^6R^7$, —$N(R^6)S(O_2)R^9$, and —$N(R^6)C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^4$ is independently selected from the group consisting of H, halo, —CN, —$NHC(O)R^6$, —$NHSO_2R^9$, —$NR^5R^6$, —$OR^5$, —$C(O)R^6$, —$C(O_2)R^6$, —$C(O)NR^6R^7$; and alkyl, alkoxy, alkenyl, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^5$ is selected from the group consisting of H, —$C(O)OR^6$, —$SO_2R^9$, —$C(O)NR^6R^7$, and alkyl, cycloalkyl, aryl, arylalkyl, heteroaryl, heteroarylalkyl, heterocyclyl, and heterocyclylalkyl groups optionally substituted with at least one $R^8$;

$R^6$ and $R^7$ are independently selected from the group consisting of H and alkyl, cycloalkyl, aryl, arylalkyl, heteroaryl, heteroarylalkyl, heterocyclyl, and heterocyclylalkyl groups optionally substituted with at least one $R^8$; or $R^5$ and $R^6$ or $R^6$ and $R^7$, when attached to the same nitrogen atom, optionally taken together with the nitrogen atom form a 3-8 membered heterocyclic ring containing 0-3 heteroatoms independently selected from O, N or S in addition to said nitrogen atom;

$R^8$ is selected from the group consisting of H, halo, —$OR^5$, —$NO_2$, —CN, —$NR^6C(O)R^7$, —$NR^6SO_2R^9$, —$NR^5R^6$, —$C(O)R^6$, —$C(O)OR^6$, —$C(O)NR^6R^7$, —$S(O_2)NR^6R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one of halo, —CN, —$NO_2$, —$OR^5$, —$SR^9$, —$NR^6R^7$, —$C(O)R^6$, —$C(O_2)R^6$, —$OC(O)R^6$, —$C(O)NR^5R^7$, —$N(R^6)C(O)R^7$, —$OS(O_2)R^9$, —$S(O_2)R^9$, —$S(O_2)NR^6R^7$, —$N(R^6)C(O)NR^6R^7$, and —$NR^6SO_2R^9$;

$R^9$ is selected from the group consisting of alkyl, cycloalkyl, aryl, arylalkyl, heteroaryl, heteroarylalkyl, heterocyclyl, and heterocyclylalkyl groups optionally substituted with at least one $R^8$;

$R^{10}$ is selected from the group consisting of H, —$C(O)R^6$, —$C(O)OR^6$, —$SO_2R^9$, —$C(O)NR^6R^7$, and alkyl, cycloalkyl, aryl, arylalkyl, heteroaryl, heteroarylalkyl, heterocyclyl, and heterocyclylalkyl groups optionally substituted with at least one $R^8$;

A is selected from the group consisting of $CHR^4$, $CR^4$, O, S, N, $NR^4$, C=O, and C=S;

B is selected from the group consisting of N, $NR^4$, $CHR^4$, $CR^4$, O, S, C=O, and C=S;

D is selected from the group consisting of $CHR^4$, O, S, and $NR^4$; and m is 1-3.

In another aspect, the present invention discloses a compound of formula II:

formula II or a pharmaceutically acceptable salt or solvate thereof, wherein:

W is S, O, or $N(R^{10})$;
X is N or $CR^3$;
Y is N or $CR^2$;
$J_1$ and $J_2$ are each independently $C(R^4)$ or N;
$R^1$ is selected from the group consisting of —H, —$NR^5R^6$, —$OR^5$, —$SR^9$, —CN, —$C(O)R^6$, —$C(O_2)R^6$, —$OC(O)R^6$, —$C(O)NR^6R^7$, —$N(R^6)C(O)R^7$, —$S(O_2)NR^6R^7$—$N(R^6)S(O_2)R^9$, —$N(R^6)C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^2$ and $R^3$ are each independently selected from the group consisting of H, halo, —CN, —$NO_2$, —$OR^5$, —$SR^9$, —$NR^5R^6$, —$C(O)R^6$, —$C(O_2)R^6$, —$OC(O)R^6$, —$C(O)NR^6R^7$, —$N(R^6)C(O)R^7$, —$OS(O_2)R^9$, —$S(O_2)R^9$, —$S(O_2)NR^6R^7$, —$N(R^6)S(O_2)R^9$, and —$N(R^6)C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^5$ is selected from the group consisting of H, —$C(O)OR^6$, —$SO_2R^9$, —$C(O)NR^6R^7$, and alkyl, cycloalkyl, aryl, arylalkyl, heteroaryl, heteroarylalkyl, heterocyclyl, and heterocyclylalkyl groups optionally substituted with at least one $R^8$;

$R^6$ and $R^7$ are independently selected from the group consisting of H and alkyl, cycloalkyl, aryl, arylalkyl, heteroaryl, heteroarylalkyl, heterocyclyl, and heterocyclylalkyl groups optionally substituted with at least one $R^8$; or $R^5$ and $R^6$ or $R^6$ and $R^7$, when attached to the same nitrogen atom, optionally taken together with the nitrogen atom form a 3-8 membered heterocyclic ring containing 0-3 heteroatoms independently selected from O, N or S in addition to said nitrogen atom;

$R^8$ is selected from the group consisting of H, halo, —$OR^5$, —$NO_2$, —CN, —$NR^6C(O)R^7$, —$NR^6SO_2R^9$, —$NR^5R^6$, —$C(O)R^6$, —$C(O)OR^6$, —$C(O)NR^6R^7$, —$S(O_2)NR^6R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one of halo, —CN, —$NO_2$, —$OR^5$, —$SR^9$, —$NR^6R^7$, —$C(O)R^6$, —$C(O_2)R^6$, —$OC(O)R^6$, —$C(O)NR^6R^7$, —$N(R^6)C(O)R^7$, —$OS(O_2)R^9$, —$S(O_2)R^9$, —$S(O_2)NR^6R^7$, —$N(R^6)C(O)NR^6R^7$, and —$NR^6SO_2R^9$;

$R^9$ is selected from the group consisting of alkyl, cycloalkyl, aryl, arylalkyl, heteroaryl, heteroarylalkyl, heterocyclyl, and heterocyclylalkyl groups optionally substituted with at least one $R^8$;

$R^{10}$ is selected from the group consisting of H, —$C(O)R^6$, —$C(O)OR^6$, —$SO_2R^9$, —$C(O)NR^6R^7$, and alkyl, cycloalkyl, aryl, arylalkyl, heteroaryl, heteroarylalkyl, heterocyclyl, and heterocyclylalkyl groups optionally substituted with at least one $R^8$;

$R^{11}$ is halo;
$R^{12}$ is —$NR^{13}R^{14}$;
$R^{13}$ is H or alkyl; and
$R^{14}$ is alkyl substituted with a hydroxy substituent.

The compounds of formula I and II are useful as selective metabotropic glutamate receptor 1 antagonists and thus are useful in the treatment and prevention of pain (neurotropic or inflammatory), migraine, anxiety, urinary incontinence and neurodegenerative diseases such as Alzheimer's disease.

DETAILED DESCRIPTION

In one embodiment, the present invention discloses tetracyclic compounds which are represented by structural formula I or II or a pharmaceutically acceptable salt, solvate or ester thereof, wherein the various moieties are as described above.

In one embodiment, in formula I, is selected from the group consisting of:
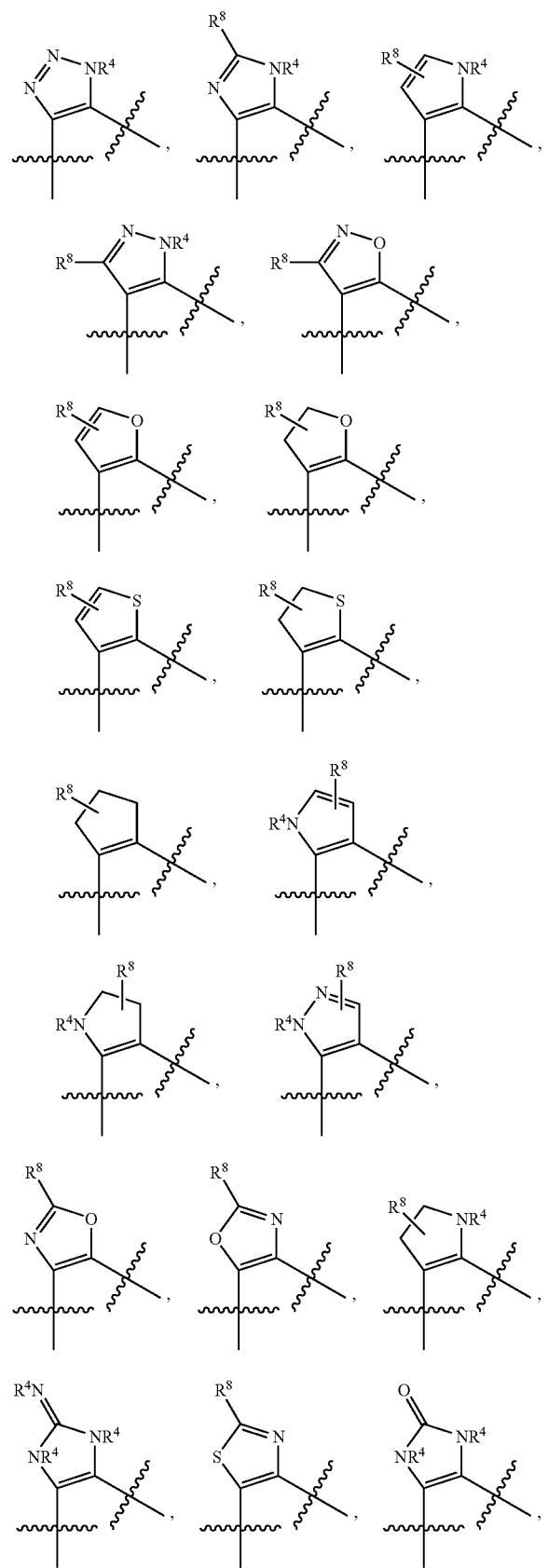
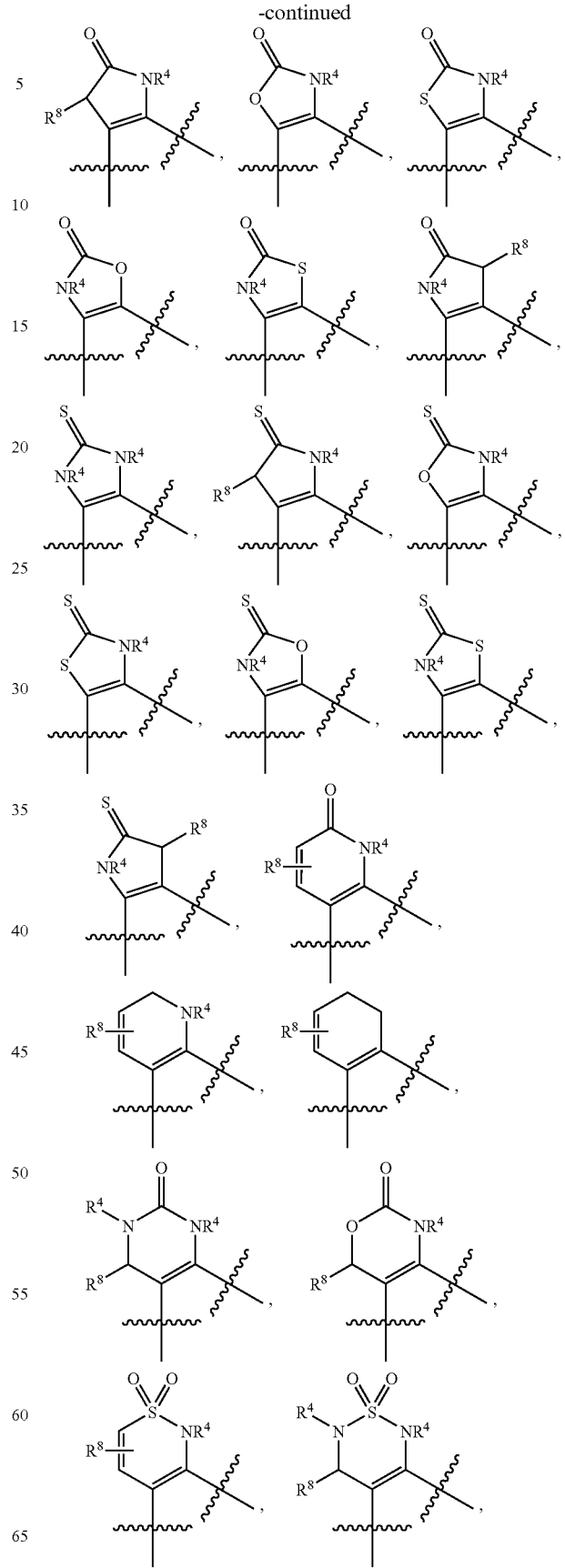

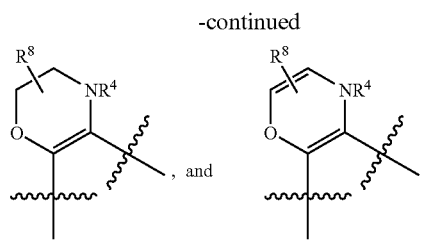, and
In another embodiment, in formula I,
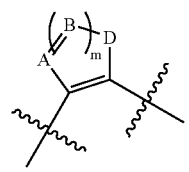
is selected from the group consisting of:
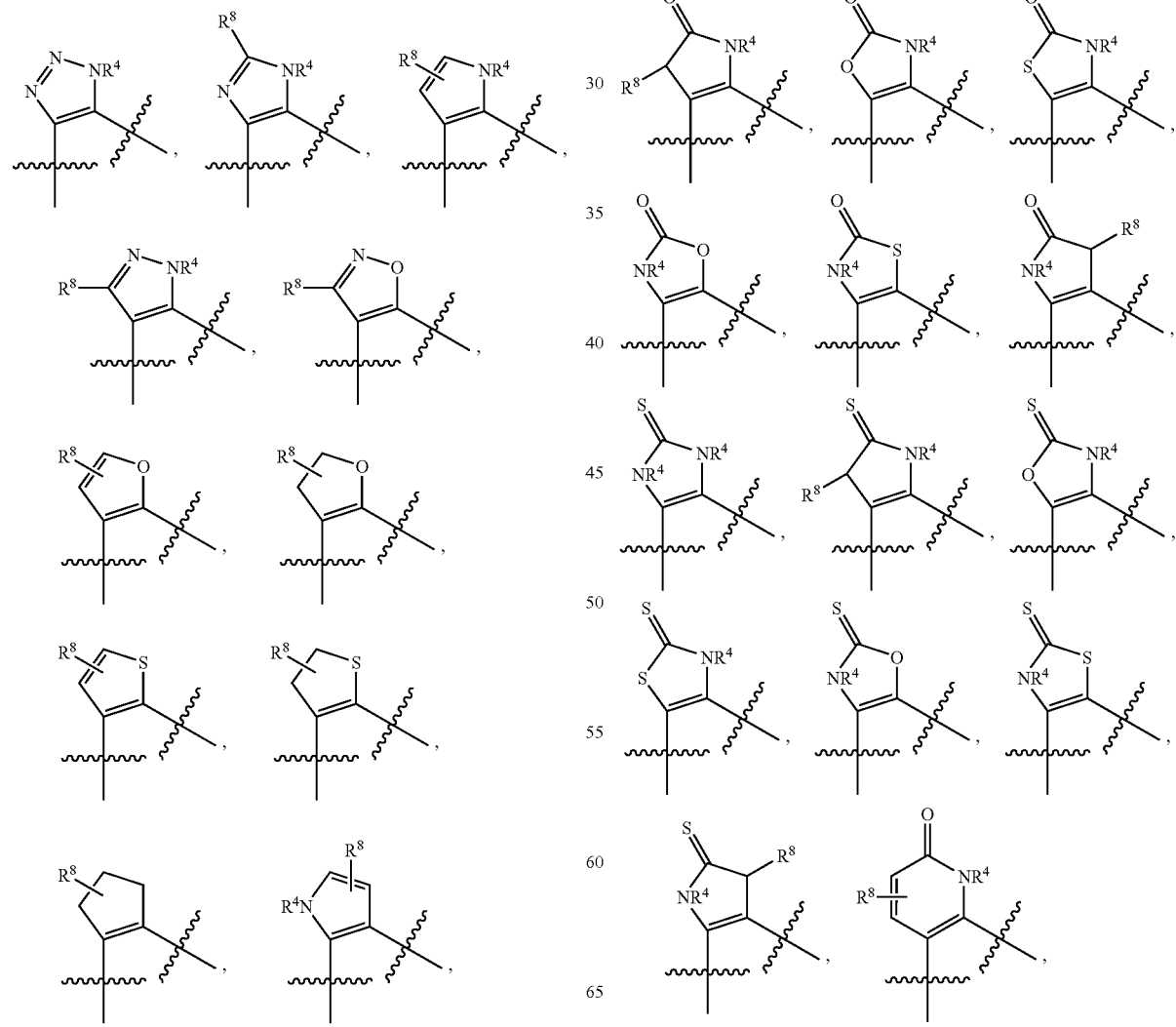

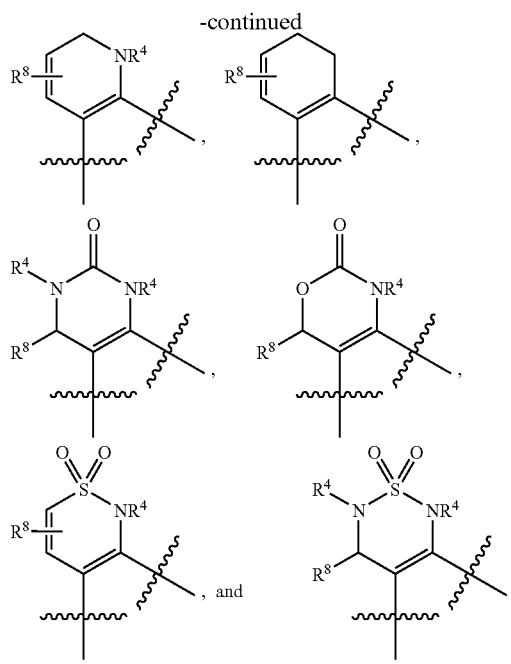

In another embodiment, in formula I or II, W is S and Z and X are N.

In another embodiment, in formula I or II, W is S, $J^1$ is $CR^4$, $J^2$ is N.

In another embodiment, in formula I or II, W is S, $J^1$ is $CR^4$, $J^2$ is N, Z and X are N.

In another embodiment, in formula I, A and B are selected from the group consisting of $CHR^4$ and $CR^4$, and D is $NR^4$.

In another embodiment, in formula I, A is $CHR^4$ or $CR^4$, B is N or $NR^4$; and D is $NR^4$.

In another embodiment, in formula I, A is N or $NR^4$, D is $NR^4$, and B is $CHR^4$ or $CR^4$.

In another embodiment, in formula I, A and B are selected from the group consisting of $CHR^4$ and $CR^4$, and D is O.

In another embodiment, in formula I, A and B are selected from the group consisting of $CHR^4$ and $CR^4$, and D is S.

In another embodiment, in formula I, A and B are selected from the group consisting of $CHR^4$ and $CR^4$ and D are $CR^4$.

In another embodiment, in formula I, A is N or $NR^4$, B is $CHR^4$ or $CR^4$, and D is $NR^4$.

In another embodiment, in formula I, A is O, B is $CHR^4$ or $CR^4$, and D is $NR^4$.

In another embodiment, in formula I, A is S, B is selected from the group consisting of C=O, C=S, and C—S—$R^9$, and D is $NR^4$.

In another embodiment, in formula I or II, W is S and $R^1$ is cyclohexyl.

In another embodiment, in formula I or II, W is S and $R^1$ is p-methylphenyl.

In another embodiment, in formula I or II, W is S and $R^1$ is p-methoxyphenyl.

In another embodiment, in formula I or II, W is S and $R^1$ is p-halophenyl.

A list of representative compounds of the present invention is shown in Table 1 below.

TABLE 1

| No | Structure |
|---|---|
| 4 | 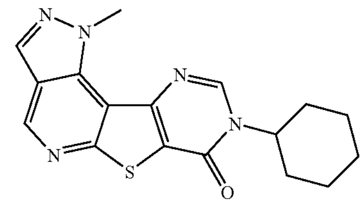 |
| 6 | 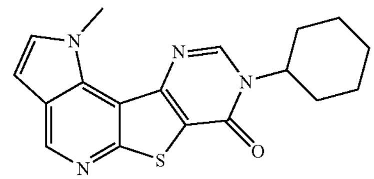 |
| 9 | 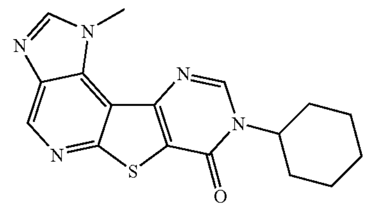 |
| 12 | 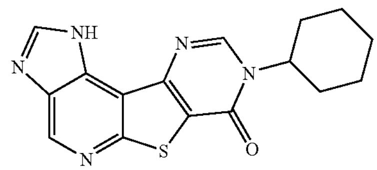 |
| 13 | 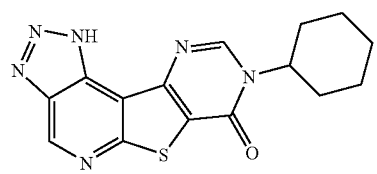 |
| 20a | 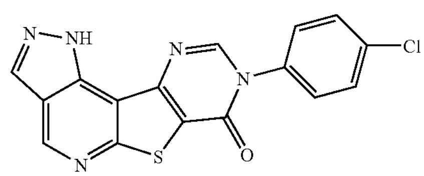 |
| 20b | 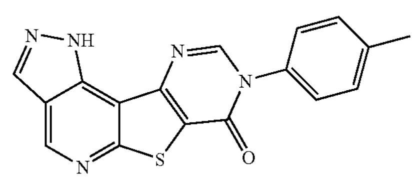 |
| 24 | 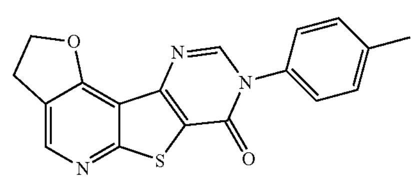 |

TABLE 1-continued

| No | Structure |
|---|---|
| 27a | 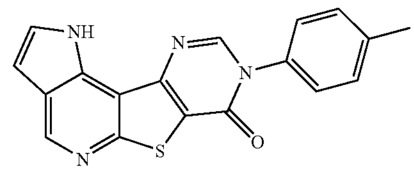 |
| 27b | 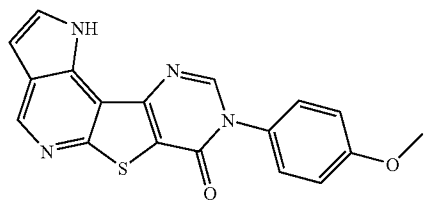 |
| 28 | 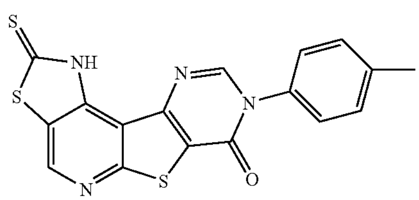 |
| 29 | 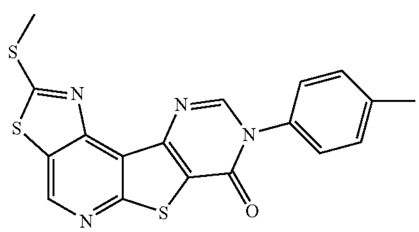 |
| 30 | 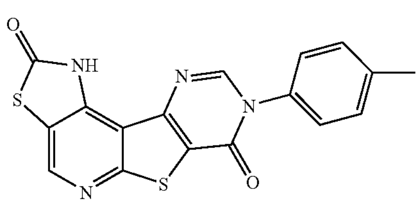 |
| 31 | 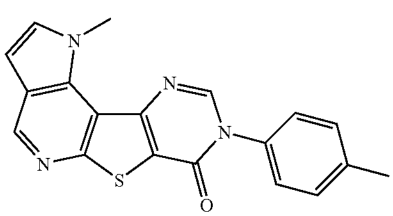 |
| 34 | 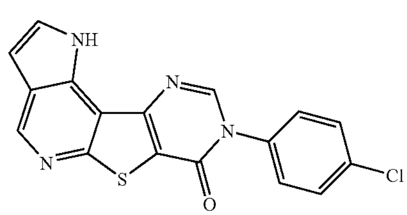 |
| 35 | |
| 36 | |
| 37a | |
| 37b | |
| 37c | |
| 37d | |

TABLE 1-continued

| No | Structure |
|---|---|
| 37e | [structure] |
| 37f | [structure] |
| 38a | [structure] |
| 38b | [structure] |
| 38c | [structure] |
| 38d | [structure] |
| 38e | [structure] |
| 38f | [structure] |
| 38g | [structure] |
| 38h | [structure] |
| 38i | [structure] |

Pharmaceutically acceptable salts, solvates or esters of the compounds of Table 1 are also contemplated.

Preferred compounds include compound numbers 20b, 27a, 27b, 34, 35, 36, 37a, 38a, 38b, 38c, 38d, 38e, 38f, 38g, 38h, and 38i.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy, —C(O)O-alkyl and —S(alkyl). Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Alkylene" means a difunctional group obtained by removal of a hydrogen atom from an alkyl group that is defined above. Non-limiting examples of alkylene include methylene, ethylene and propylene.

"Aryl" (sometimes abbreviated "ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. "Cycloalkyl" includes "arylcycloalkyl" and "cycloalkylaryl" as defined below.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above.

"Cyanoalkyl" means an alkyl as defined above wherein one or more hydrogen atoms on the alkyl is replaced by a cyano group.

"Oxo" means (=O) and "thioxo" means (=S).

"Ring system substituent" means a substituent attached to an aromatic or non-aromatic ring system which, for example, replaces an available hydrogen on the ring system. Ring system substituents may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl. "Ring system substituent" also means a cyclic ring of 3 to 7 ring atoms of which 1-2 may be a heteroatom, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

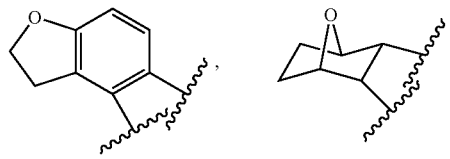

and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl. "Cycloalkenyl" includes "arylcycloalkenyl" and "cycloalkenylaryl" as defined below.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. A non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. "Heterocyclyl" includes "heteroarylcycloalkyl" and "cycloalkylheteroaryl" as defined below.

"Arylcycloalkenyl" means a group derived from a fused aryl and cycloalkenyl as defined herein by removal of a hydrogen atom from the cycloalkenyl portion. Preferred arylcycloalkenyls are those wherein aryl is phenyl and the cycloalkenyl consists of about 5 to about 6 ring atoms. The arylcycloalkenyl can be optionally substituted by one or more ring system substituents, wherein "ring system substituent" is as defined above. Non-limiting examples of suitable arylcycloalkenyls include 1,2-dihydronaphthalene, indene, and the like. The bond to the parent moiety is through a non-aromatic carbon atom.

"Cycloalkenylaryl" means a group derived from a fused arylcycloalkenyl as defined herein by removal of hydrogen atom from the aryl portion. Non-limiting examples of suitable cycloalkenylaryls are as described herein for a arylcycloalkenyl, except that the bond to the parent moiety is through an aromatic carbon atom.

"Arylcycloalkyl" means a group derived from a fused aryl and cycloalkyl as defined herein by removal of a hydrogen atom from the cycloalkyl portion. Preferred arylcycloalkyls are those wherein aryl is phenyl and the cycloalkyl consists of about 5 to about 6 ring atoms. The arylcycloalkyl can be optionally substituted by one or more ring system substituents, wherein "ring system substituent" is as defined above. Non-limiting examples of suitable arylcycloalkyls include 1,2,3,4-tetrahydronaphthyl, and the like. The bond to the parent moiety is through a non-aromatic carbon atom.

"Cycloalkylaryl" means a group derived from a fused arylcycloalkyl as defined herein by removal of a hydrogen atom from the aryl portion. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl as defined herein by removal of a hydrogen atom from the cycloalkyl portion. Preferred heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The heteroarylcycloalkyl can be optionally substituted by one or more ring system substituents, wherein "ring system substituent" is as defined above. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like. The bond to the parent moiety is through a non-aromatic carbon atom.

"Cycloalkylheteroaryl" means a group derived from a fused beteroarylcycloalkyl as defined herein by removal of a hydrogen atom from the heteroaryl portion. Non-limiting examples of suitable cycloalkylheteroaryls are as described herein for heteroarylcycloalkyl, except that the bond to the parent moiety is through an aromatic carbon atom.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkynyl" means an aryl-alkynyl-group in which the aryl and alkynyl are as previously described. Preferred aralkynyls contain a lower alkynyl group. The bond to the parent moiety is through the alkynyl. Non-limiting examples of suitable aralkynyl groups include phenacetylenyl and naphthylacetylenyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Heteroaralkynyl" means a heteroaryl-alkynyl-group in which the heteroaryl and alkynyl are as previously described. Preferred heteroaralkynyls contain a lower alkynyl group. Non-limiting examples of suitable heteroaralkynyl groups include pyrid-3-ylacetylenyl and quinolin-3-ylacetylenyl. The bond to the parent moiety is through the alkynyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Heteroaroyl" means a heteroaryl-C(O)— group in which the heteroaryl group is as previously described. Non-limiting examples of suitable groups include nicotinoyl and pyrrol-2-ylcarbonyl. The bond to the parent moiety is through the carbonyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups are as previously described. Non-limiting examples of suitable aralkyloxy groups include benzyloxy and 1- or 2-naphthalenemethoxy. The bond to the parent moiety is through the ether oxygen.

"Alkylamino" means an —NH$_2$ or —NH$_3^+$ group in which one or more of the hydrogen atoms on the nitrogen is replaced by an alkyl group as defined above.

"Arylamino" means an —NH$_2$ or —NH$_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. A non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O$_2$)— group. The bond to the parent moiety is through the sulfonyl.

"Arylsulfinyl" means an aryl-S(O)— group. The bond to the parent moiety is through the sulfinyl.

It is noted that carbons of formula I can be replaced with 1-3 silicon atoms, provided all valency requirements are satisfied.

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

When any variable (e.g., aryl, heterocycle, R$^2$, etc.) occurs more than one time in any constituent or formula, its definition on each occurrence is independent of its definition at every other occurrence.

As used herein, the term "composition" is intended to encompass a product comprising the specified ingredients in the specified amounts, as well as any product which results, directly or indirectly, from a combination of the specified ingredients in the specified amounts.

Lines drawn into the ring systems, such as, for example:

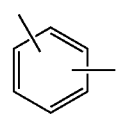

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

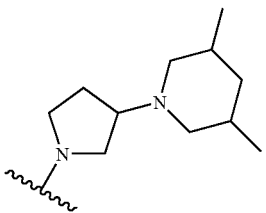

represents

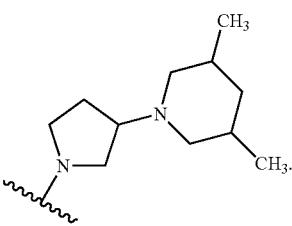

It should also be noted that any carbon or heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or II or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of formula I or II or a pharmaceutically acceptable salt, hydrate or solvate or ester of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$) alkyl, and the like.

Similarly, if a compound of formula I or II contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of formula I or II incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ ishours ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino($C_1$-$C_4$)alkyl or mono-N- or di-N,N-($C_1$-$C_6$)alkylaminoalkyl, —C(Y$^4$)Y$^5$ wherein Y$^4$ ishouror methyl and Y$^5$ is mono-N- or di-N,N-($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of a compound or a composition of the present invention effective in antagonizing mGluRs, in particular mGluR1, and thus producing the desired therapeutic, ameliorative, inhibitory or preventative effect in a suitable patient.

"Capsule" is meant to describe a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet" is meant to describe a compressed or molded solid dosage form containing the active ingredients with suitable diluents. The tablet can be prepared by compression of mixtures or granulations obtained by wet granulation, dry granulation or by compaction.

"Oral gels" is meant to describe to the active ingredients dispersed or solubilized in a hydrophillic semi-solid matrix.

"Powders for constitution" refers to powder blends containing the active ingredients and suitable diluents which can be suspended in water or juices.

"Diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Disintegrants" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

"Binders" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

"Lubricant" is meant to describe a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

"Glidents" means materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

"Coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

"Bioavailability" refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds of formula I and II form salts which are also within the scope of this invention. Reference to a compound of formula I or II herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I or II contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I or II may be formed, for example, by reacting a compound of formula I or II with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al., *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of formula I, II, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. For example, if a compound of formula I or II incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester, and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of formula I or II may be atropisomers (e.g., substituted biaryls) and are considered as part of this invention. Enantiomers can also be separated by use of chiral HPLC column.

Polymorphic forms of the compounds of formula I and II, and of the salts, solvates, esters and prodrugs of the compounds of formula I and II, are intended to be included in the present invention The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of formula I or II (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of formula I or II can generally be prepared by following procedures analogous to those disclosed in the Schemes and/or in the Examples hereinbelow, by substituting an appropriate isotopically labelled reagent for a non-isotopically labelled reagent.

The compounds according to the invention have pharmacological properties; in particular, the compounds of formula I or II can be mGluR (metabotropic glutamate receptor) antagonists, more particularly, selective mGluR1 antagonists. Accordingly, the present compounds are useful in the treatment or prevention of conditions that are treatable or preventable by inhibiting mGluR, more particularly, mGluR1 function. Such conditions include a variety of acute and chronic neurological disorders associated with excessive or inappropriate stimulation of excitatory amino acid transmission as well as conditions which lead to glutamate-deficient functions.

Examples of treatable or preventable acute neurological disorders include, but are not limited to, cerebral deficits subsequent to cardiac bypass surgery and grafting, cerebral ischemia, stroke (ischemic or hemorrhagic), spinal cord injuries (due to trauma, infarction/ischemia or inflammation), head trauma, perinatal hypoxia, cardiac arrest and hypoglycemic neuronal damage. Examples of treatable or preventable chronic neurological disorders include, but are not limited to, Alzheimer's disease, Huntington's Chorea, amyotrophic lateral sclerosis (ALS), AIDS-induced dementia, inherited ataxias, ocular damage and retinopathy, cognitive disorders, and idiopathic and drug-induced Parkinson's. Other conditions associated with glutamate dysfunctions treatable or preventable by compounds of formula I or II include, but are not limited to, muscle spasms, convulsions (e.g., epilepsy), spasticity, migraine (including menstrual migraine), psychoses (e.g., schizophrenia and bipolar disorder), urinary incontinence, anxiety and related disorders (e.g. panic attack), emesis, brain edema, tardive dyskinesia, depression, drug tolerance and withdrawal (e.g., opiates, benzodiazepines, nicotine, cocaine, or ethanol), and smoking cessation.

The compounds of formula I or II are also useful for treating or preventing pain which may be neuropathic (nerve damage) or inflammatory (tissue damage). These compounds are particularly useful for treating or preventing neuropathic pain. Neuropathic pain used herein refers to an abnormal state of pain sensation, in which a reduction of pain threshold and the like are continued, due to functional abnormalities accompanying damage or degeneration of a nerve, plexus or perineural soft tissue, which is caused by wound, compression, infection, cancer, ischemia and the like, or metabolic disorders such as diabetes mellitus and the like. Neuropathic pain includes pain caused by either central or peripheral nerve damage. It also includes the pain caused by either mononeuropathy or polyneuropathy. In some embodiments, the neuropathic pain is induced by diabetes. In other embodiments, the neuropathic pain is induced by compression of nerves.

Examples of neuropathic pain treatable or preventable by the present compounds include, but are not limited to, allodynia (a pain sensation induced by mechanical or thermal stimulus that does not normally provoke pain), hyperalgesia (an excessive response to a stimulus that is normally painful), hyperesthesia (an excessive response to a contact stimulus), diabetic polyneuropathy, entrapment neuropathy, cancer pain, central pain, labor pain, myocardial infarction pain, post-stroke pain, pancreatic pain, colic pain, muscle pain, post-operative pain, pain associated with intensive care, pain associated with a periodontal disease (including gingivitis and periodontitis), menstrual pain, migraine pain, persistent headaches (e.g., cluster headache or chronic tension headache), persistent pain states (e.g., fibromyalgia or myofascial pain), trigeminal neuralgia, postherpetic neuralgia, arthritic pain (e.g., pain due to osteoarthritis or rheumatoid arthritis), bursitis, pain associated with AIDS, visceral pain (e.g., interstitial cystitis and irritable bowel syndrome (IBS)), pain due to spinal trauma and/or degeneration, burn pain, referred pain, enhanced memory of pain and neuronal mechanisms involved in coping with pain. The compounds of the present invention are particularly useful for treating or preventing allodynia and hyperalgesia.

Compounds of formula I or II are also useful for treating or preventing pain associated with inflammation or an inflammatory disease in a patient. The pain associated with inflammation or an inflammatory disease treatable or preventable by the present compounds may arise where there is an inflammation of the body tissue which may be a local inflammatory response and/or a systemic inflammation. For example, the present compounds can be used to treat or prevent pain associated with inflammatory diseases including, but not limited to, organ transplant rejection; reoxygenation injury resulting from organ transplantation including transplantation of the heart, lung, liver, or kidney; chronic inflammatory diseases of the joints, including arthritis, rheumatoid arthritis, osteoarthritis and bone diseases associated with increased bone resorption; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection and necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer.

The present compounds can also be used for treating or preventing pain associated with an inflammatory disease that involves a systemic inflammation of the body, such as gram-positive or gram negative shock, hemorrhagic or anaphylactic shock, shock induced by cancer chemotherapy in response to pro-inflammatory cytokines (e.g., shock associated with pro-inflammatory cytokines), and shock induced by a chemotherapeutic agent that is administered as a treatment for cancer.

One aspect of this invention relates to a method of selectively antagonizing mGluR1 in a cell in need thereof, comprising contacting said cell with at least one compound of formula I or II or a pharmaceutically acceptable salt or solvate thereof.

The term "antagonist of metabatropic glutamate receptor (e.g., mGluR1)" refers to a compound that binds to the metabatropic glutamate receptor (e.g., mGluR1) but fails to elicit a response thereby blocking agonist action, i.e, inhibiting a function of mGluRs (e.g., mGluR1). Accordingly, mGluR (e.g., mGluR1) mediated processes and responses can be inhibited with an antagonist of mGluR (e.g., mGluR1). Preferably, an antagonist selectively antagonizes group I mGluRs. More preferably, an antagonist of the present invention is a selective antagonist of mGluR1. A selective antagonist of mGluR1 is one that antagonizes mGluR1, but antagonizes other mGluRs only weakly or substantially not at all, or at least antagonizes other mGluRs with an $IC_{50}$ at least 10 or even 100 or 1000 times greater than the $IC_{50}$ at which it antagonizes mGluR1. Most preferred antagonists are those which can selectively antagonize mGluR1 at low concentrations, for example, those that cause a level of antagonism of 50% or greater at a concentration of 100 nM or less.

Another aspect of this invention relates to a method of treating or preventing a disease or condition associated with mGluR1 in a mammal (e.g., human) in need thereof comprising administering a therapeutically effective amount of at least one compound of formula I or II or a pharmaceutically acceptable salt or solvate thereof to said mammal.

A preferred dosage is about 0.001 to 500 mg/kg of body weight/day of the compound of formula I or II. An especially preferred dosage is about 0.01 to 25 mg/kg of body weight/ day of a compound of formula I or II or a pharmaceutically acceptable salt or solvate thereof.

The compounds of this invention may also be useful in combination (administered together or sequentially) with one or more additional therapeutic agents for the treatment of the above disorders or conditions. Such additional therapeutic agents may be a pain management agent, including non-opioid analgesics such as acetylsalicylic acid, choline magnesium trisalicylate, acetaminophen, ibuprofen, fenoprofen, diflusinal, and naproxen; and opioid analgesics, such as morphine, hydromorphone, methadone, levorphanol, fentanyl, oxycodone, and oxymorphone. Other such therapeutic agents may be a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing urinary incontinence (UI), an agent for treating Alzheimer's disease, an agent for treating or preventing inflammatory bowel disease (IBD), an agent for treating or preventing inflammatory bowel syndrome (IBS), an agent for treating Parkinson's disease and parkinsonism, an agent for treating anxiety, an agent for treating epilepsy, an agent for treating a stroke, an agent for treating psychosis, an agent for treating Huntington's chorea, an agent for treating ALS, an agent for treating vomiting, an agent for treating dyskinesia, or an agent for treating depression, and mixtures thereof.

If formulated as a fixed dose, such combination products employ the compounds of this invention within the dosage range described herein and the other pharmaceutically active agent or treatment within its dosage range. Compounds of formula I or II may also be administered sequentially with known therapeutic agents when a combination formulation is inappropriate. The invention is not limited in the sequence of administration; compounds of formula I or II may be administered either prior to or after administration of the known therapeutic agent. Such techniques are within the skills of persons skilled in the art as well as attending physicians.

Accordingly, in one aspect, this invention includes combinations comprising an amount of at least one compound of formula I or II or a pharmaceutically acceptable salt or solvate thereof, and an amount of one or more additional therapeutic agents listed above wherein the amounts of the compounds/treatments result in a desired therapeutic effect.

The pharmacological properties of the compounds of this invention may be confirmed by a number of pharmacological assays. The selective antagonistic activity of the present compounds towards the metabotropic glutamate receptor 1 (mGluR1) may be assayed by methods known in the art, for example, by using the methods as described in the examples.

The actions of the compounds of formula I or II for the treatment or prevention of pain may be assessed by various animal models, for example, by the following tests:

Formalin test: Mice are gently restrained and 30 μl of formalin solution (1.5% in saline) is injected subcutaneously into the plantar surface of the right hind paw of the mouse, using a microsyringe with a 27 gauge needle. After the formalin injection, the mouse is immediately put back into the Plexiglas observation chamber (30×20×20 cm) and the nociceptive response of the animal to formalin injection is observed for a period of 60 min. The duration of licking and flinching of the injected paw is recorded and quantified every 5 min for the total observation period. The recording of the early phase (first phase) starts immediately and lasts for 5 min. The late phase (second phase) starts about 10-15 min after formalin injection.

L5 and L6 spinal nerve ligation of the sciatic nerve (neuropathic pain model): The peripheral neuropathy is produced by ligating the L5 and L6 spinal nerves of the right sciatic nerve, according to the method previously described by Kim and Chung (1992) except for small changes. Briefly, rats are anaesthetized with chloral hydrate (400 mg/kg, i.p.), placed in a prone position and the right paraspinal muscles separated from the spinous processes at the L4-S2 levels. The L5 transverse process is carefully removed with a small rongeur to identify the L4-L5 spinal nerves. The right L5 and L6 spinal nerves are isolated and tightly ligated with 7/0 silk thread. A complete hemostasis is confirmed and the wound sutured.

Chronic constriction injury (CCI) of the sciatic nerve (neuropathic pain model): Surgery is performed according to the method described by Bennett & Xie (1987). Rats are anaesthetized with chloral hydrate (400 mg/kg, i.p.) and the common sciatic nerve is exposed at the level of the mid-thigh. Proximally, at about 1 cm from the nerve trifurcation, four loose ligatures (4/0 silk) spaced 1 mm are tied around the nerve. The ligature delays, but does not arrest, circulation through the superficial epineural vasculature. The same procedure is performed except for ligature placement (sham surgery) in a second group of animals.

Carrageenan (inflammatory pain model): The right hind paw of each animal is injected at subplantar level with 0.1 mL of carrageenan (25 GA needle). Pre-tests are determined prior to carrageenan or drug administration. In POST-TREATMENT protocol, rats are tested 3 hours after carrageenan treatment to establish the presence of hyperalgesia and then at different times after drug administration. In PRE-TREATMENT protocol, one hour after drug administration, rats are treated with carrageenan and they are tested starting from 3 hours later.

Freund's adjuvant-induced arthritic model (inflammatory pain model): Animals receive a single subplantar injection of 100 mL of a 500 mg dose of heat-killed and dried *Mycobacterium tuberculosis* (H37 Ra, Difco Laboratories, Detroit, Mich., USA) in a mixture of paraffin oil and an emulsifying agent, mannide monooleate (complete Freund's adjuvant). Control animals are injected with 0.1 mL mineral oil (incomplete Freund's adjuvant).

Measurement of tactile allodynia (behavioural test): Behavioral tests are conducted by observer blinded to the treatment during the light cycle to avoid circadian rhythm fluctuation. Tactile sensitivity is evaluated using a series of calibrated Semmes-Weinstein (Stoelting, Ill.) von Frey filaments, bending force ranging from 0.25 to 15 g. Rats are placed in a transparent plastic box endowed with a metal mesh floor and are habituated to this environment before experiment initiation. The von Frey filaments are applied perpendicularly to the midplantar surface of the ipsilateral hind paws and the mechanical allodynia is determined by sequentially increasing and decreasing the stimulus strength ("up-down" paradigm of the filament presentation). Data are analysed with a Dixon non-parametric test (Chaplan et al. 1994). Paw licking or vigorously shaking after stimulation is considered pain-like responses.

Thermal hyperalgesia (behavioural test): Thermal hyperalgesia to radiant heat is assessed by measuring the withdrawal latency as an index of thermal nociception (Hargreaves et al., 1998). The plantar test (Basile, Comerio, Italy) is chosen because of its sensitivity to hyperalgesia. Briefly, the test consists of a movable infrared source placed below a glass plane onto which the rat is placed. Three individual perspex boxes allow three rats to be tested simultaneously. The infrared source is placed directly below the plantar surface of the hind paw and the paw withdrawal latency (PWL) is defined as the time taken by the rat to remove its hind paw from the heat source. PWLs are taken three times for both hind paws of each rat and the mean value for each paw represented the thermal pain threshold of rat. The radiant heat source is adjusted to result in baseline latencies of 10-12 sec. The instrument cut-off is fixed at 21 sec to prevent tissue damage.

Weight bearing (behavioural test): An incapacitance tester is employed for determination of hind paw weight distribution. Rats are placed in an angled plexiglass chamber positioned so that each hind paw rested on a separate force plate. The weight bearing test represents a direct measure of the pathological condition of the arthritic rats without applying any stress or stimulus, thus this test measures a spontaneous pain behaviour of the animals.

While it is possible for the active ingredient to be administered alone, it is preferable to present it as a pharmaceutical composition. The compositions of the present invention comprise at least one active ingredient, as defined above, together with one or more acceptable carriers, adjuvants or vehicles thereof and optionally other therapeutic agents. Each carrier, adjuvant or vehicle must be acceptable in the sense of being compatible with the other ingredients of the composition and not injurious to the mammal in need of treatment.

Accordingly, this invention also relates to pharmaceutical compositions comprising at least one compound of formula I or II, or a pharmaceutically acceptable salt, solvate or ester thereof and at least one pharmaceutically acceptable carrier, adjuvant or vehicle.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts, solvates or esters thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of formula I or II or a pharmaceutically acceptable salt, solvate, or ester thereof and at least one pharmaceutically acceptable carrier, adjuvant or vehicle.

Yet another aspect of this invention is a kit comprising an amount of at least one compound of formula I or II or a pharmaceutically acceptable salt, solvate or ester thereof and an amount of at least one additional therapeutic agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz), Varian Mercury VX-400 (400 MHz), or Bruker-Biospin AV-500 (500 MHz), and are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The following solvents and reagents may be referred to by their abbreviations in parenthesis:

Me=methyl; Et=ethyl; Pr=propyl; Bu=butyl; Ph=phenyl, and Ac=acetyl

μl=microliters

AcOEt or EtOAc=ethyl acetate

AcOH or HOAc=acetic acid

ACN=acetonitrile atm=atmosphere

Boc or BOC=tert-butoxycarbonyl

DCM or $CH_2Cl_2$: dichloromethane:

DIPEA=diisopropylethylamine

DMAP=4-dimethylaminopyridine

DMF=dimethylformamide
DMS=dimethylsulfide
DMSO=dimethyl sulfoxide
EDCl=1-(3-dimethylaminopropyl)-3-ethylcarbodiimide
Fmoc=9-fluorenylmethoxycarbonyl
g=grams
h=hour
HATU=O-(7-azabenzotriazol-1-yl)-N,N,N',N'-tetramethyluronium hexafluorophosphate
HOBt=1-hydroxybenzotriazole
LAH=lithium aluminum hydride
LCMS=liquid chromatography mass spectrometry
min=minute
mg=milligrams
mL=milliliters
mmol=millimoles
MCPBA=3-chloroperoxybenzoic acid MeOH: methanol
MS=mass spectrometry
NMR=nuclear magnetic resonance spectroscopy
RT or rt=room temperature (ambient, about 25° C.).
TEA or Et₃N=triethylamine
TFA=trifluoroacetic acid
THF=tetrahydrofuran
TLC=thin layer chromatography
TMS=trimethylsilyl
Tos or tosyl=p-toluenesulfonyl
Tr=triphenylmethyl

EXAMPLES

In general, the compounds of this invention may be prepared from known or readily prepared starting materials, following methods known to one skilled in the art and those illustrated below. All stereoisomers and tautomeric forms of the compounds are contemplated.

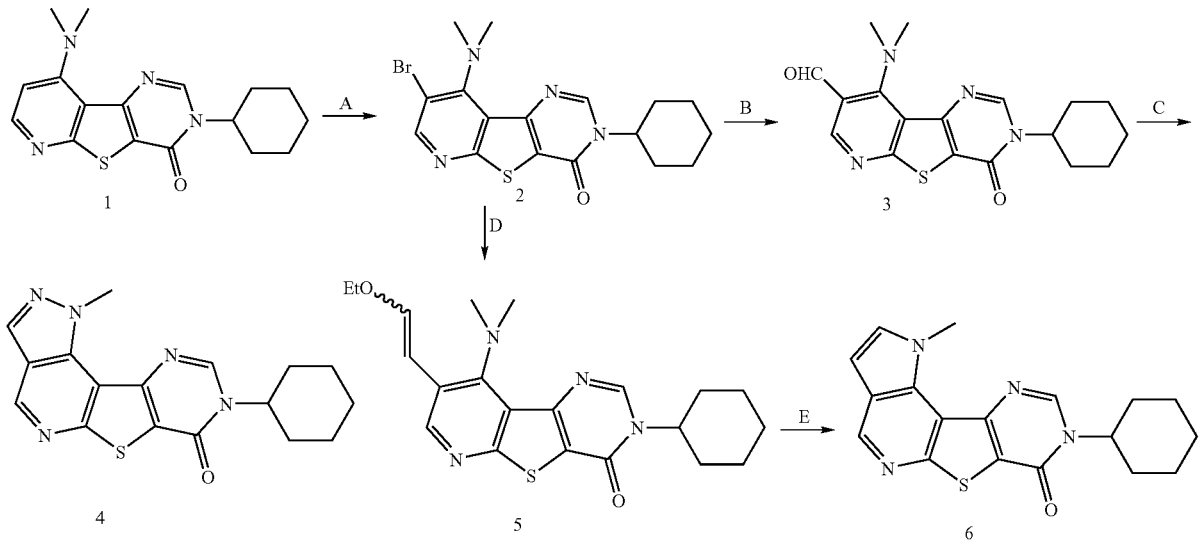

Scheme 1

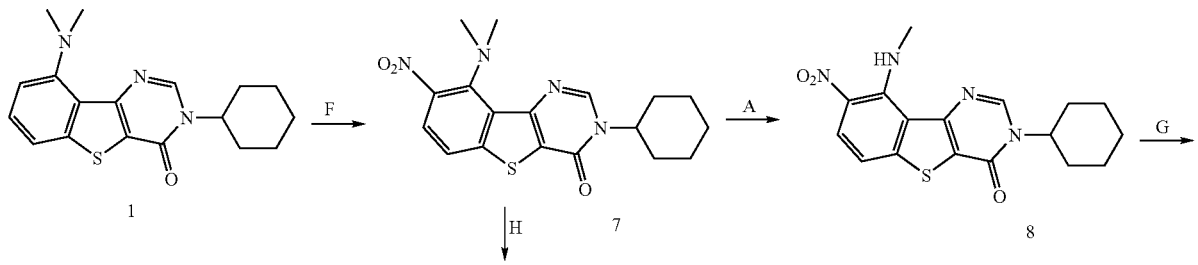

Scheme 2

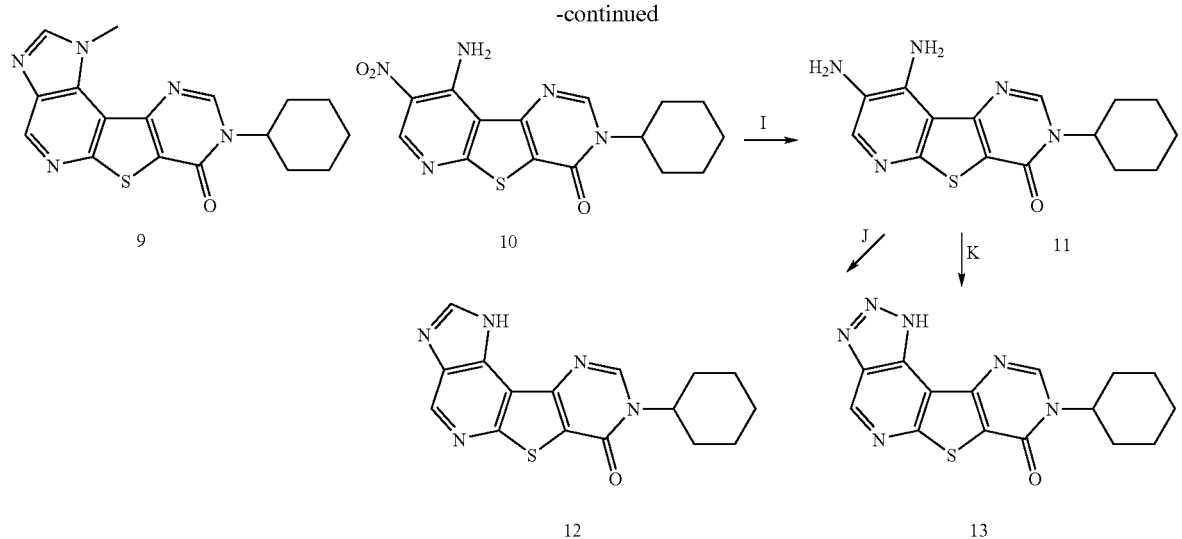
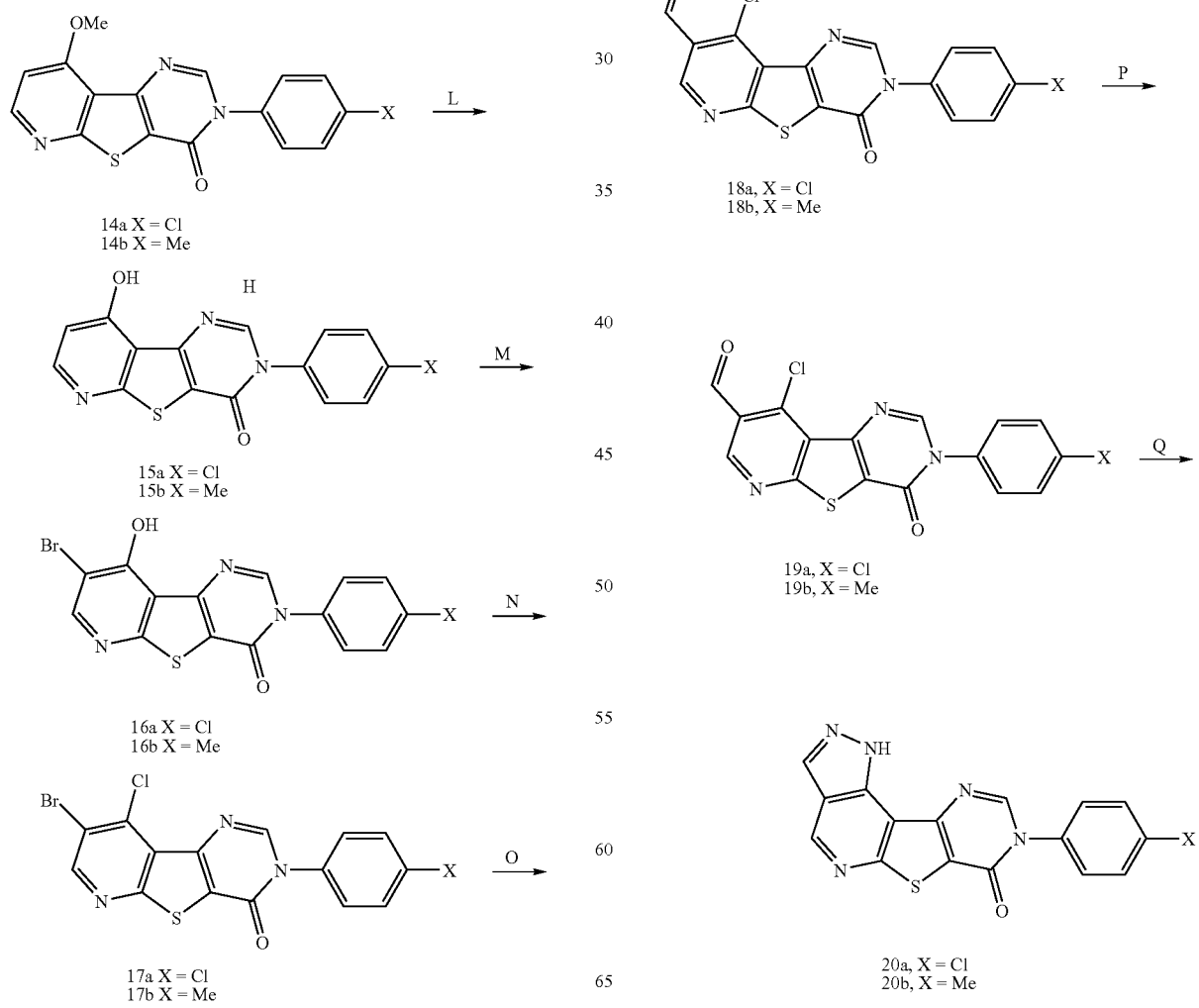
Scheme 3
14a X = Cl
14b X = Me
15a X = Cl
15b X = Me
16a X = Cl
16b X = Me
17a X = Cl
17b X = Me
18a, X = Cl
18b, X = Me
19a, X = Cl
19b, X = Me
20a, X = Cl
20b, X = Me Scheme 4
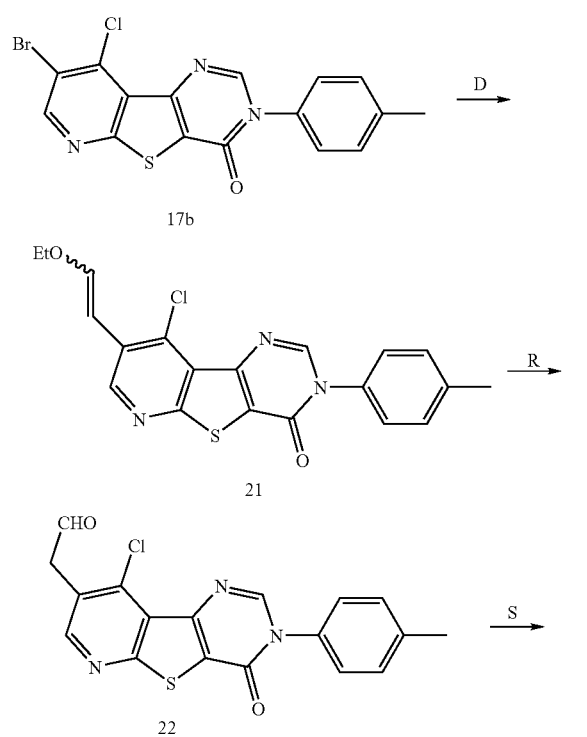
Scheme 5
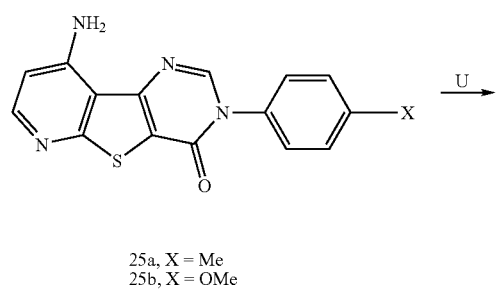
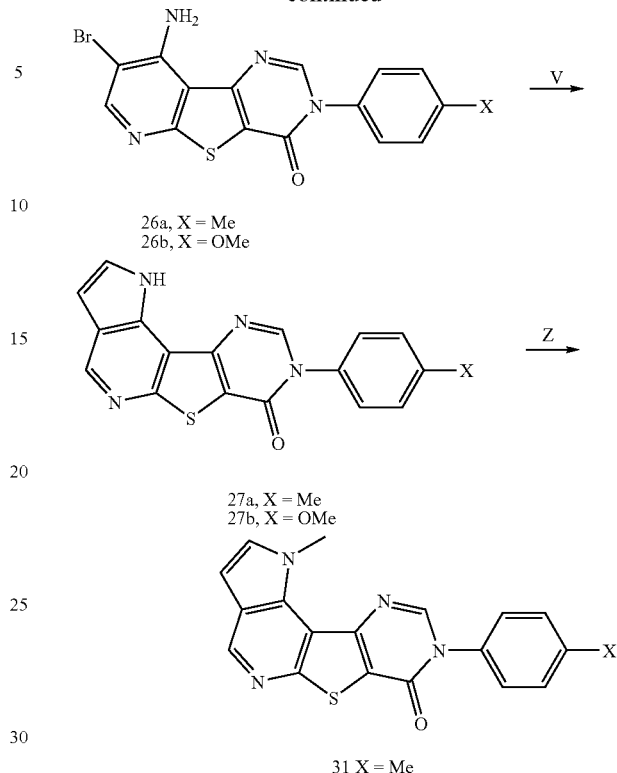
Scheme 6
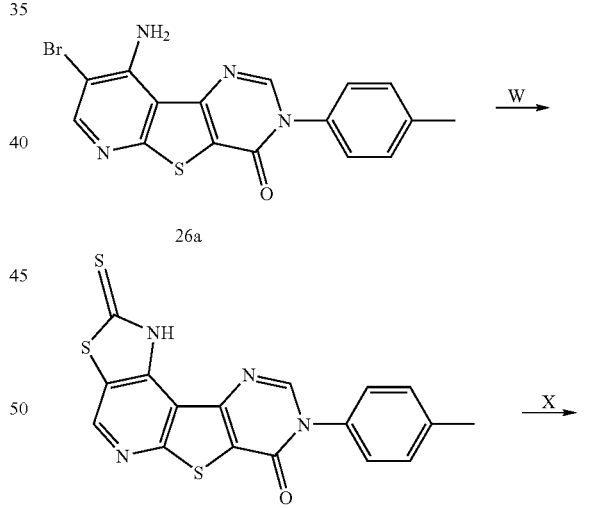

-continued

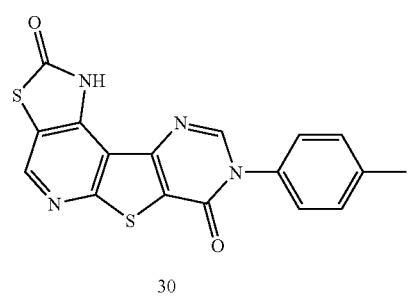

30

Scheme 7

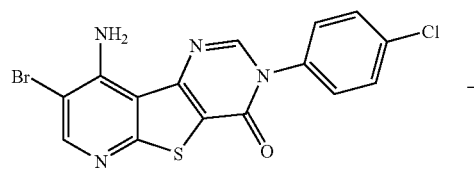

26c

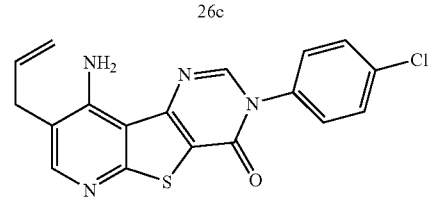

32

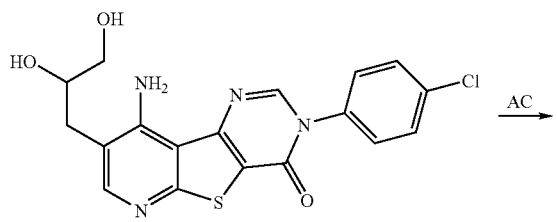

33

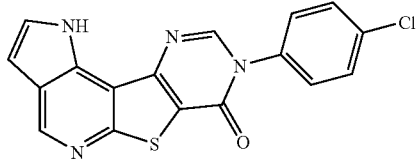

34

Scheme 8

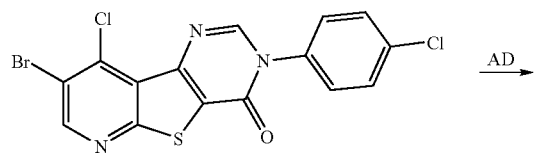

17a

-continued

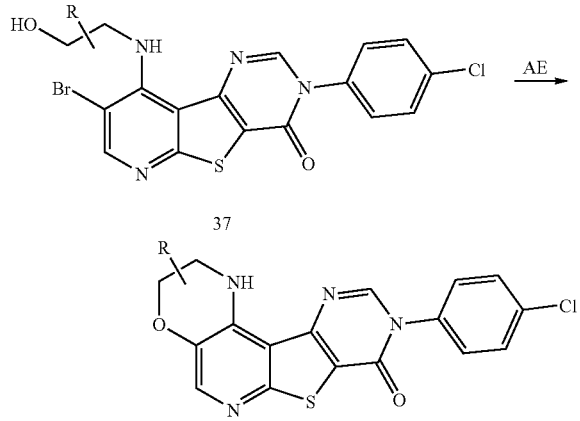

37

38

Scheme 9

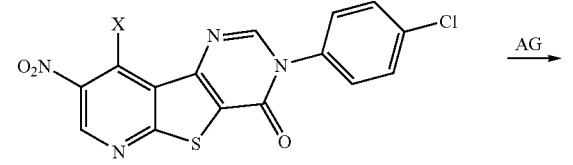

39

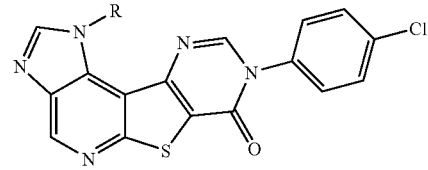

40a X = NH2
40b X = NHMe

35 R = H
36 R = Me

Other related routes/chemistry are also contemplated.

Experimental Procedures

Method A

To a solution of 0.042 g (0.12 mmol) of Compound 1 in 4 mL of acetonitrile was added a solution of 0.023 g (0.13 mmol) of N-bromosuccinimide (NBS). The mixture was stirred at the same temperature for 3 hours, and concentrated. The residue was purified by preparative TLC eluting with 4% methanol in methylene chloride to give 0.03 g of compound 2. Calculated MS for $C_{17}H_{20}BrN_4OS$=409.1. found m/z=409.0.

Compound 8 was prepared from compound 7 analogously. Calculated MS for $C_{16}H_{18}N_5O_3S$=360.1. found m/z=360.1.

Method B

To a stirred solution of 0.10 g (0.25 mmol) of compound 2 in 4 mL of ether was added 0.25 mL (0.4 mmol) of n-BuLi at −78° C. After 1 hour, a solution of 0.1 mL of DMF in 1 mL of ether was introduced. The mixture was stirred for 3 hours and quenched with 30 mL of water. It was extracted with two 30 mL portions of ethyl acetate. The combined organic extracts were washed 20 mL of brine, and concentrated. The residue was purified by preparative TLC eluting with 7% methanol in methylene chloride to give 0.03 g of compound 3. Calculated MS for $C_{18}H_{21}N_4O_2S=357.1$. found m/z=357.2.

Method C

A mixture of 0.022 g (0.06 mmol) of compound 3, 0.020 g (0.25 mmol) of methylhydrazine hydrochloride in 4 mL of t-BuOH was stirred at reflux for 2 days, and concentrated. The residue was purified by preparative TLC eluting with 4% methanol in methylene chloride to give 0.006 g of compound 4. Calculated MS for $C_{17}H_{18}N_5OS=340.1$. found m/z=340.2.

Method D

A mixture of 0.20 g (0.5 mmol) of compound 2, 0.36 g (1 mmol) of ethoxyvinyltributyltin, 0.04 g (cat.) of Pd $(PPh_3)_4$ and 0.2 g (1.5 mmol) of diisopropylethylamine in 3 mL of toluene in a sealed tube was heated at 180° C. for 20 minutes using microwave irradiation (Personalchemistry). It was concentrated; the residue was purified by chromatography eluting with 1 to 4% methanol in methylene chloride plus 1% ammonium hydroxide to give 0.13 g of compound 5. Calculated MS for $C_{21}H_{27}N_4O_2S=399.2$. found m/z 399.2.

Compound 21 was prepared from compound 17b analogously. Calculated MS for $C_{20}H_{17}ClN_3O_2S=398.1$. found m/z=398.0.

Method E

To a stirred solution of 0.10 g (0.25 mmol) of compound 5 in 6 mL of acetonitrile were added 0.375 g (2.5 mmol) of sodium iodide and 0.27 g (2.5 mmol) of chlorotrimethylsilane at room temperature. After 30 minutes, it was quenched with 30 mL of saturated sodium bicarbonate and extracted with two 40 mL portions of methylene chloride. The combined organic extracts were washed with 20 mL of brine, concentrated. The residue was purified by preparative TLC eluting with 4% methanol in methylene chloride to give 0.028 g of compound 6. Calculated MS for $C_{18}H_{19}N_4OS=339.1$. found m/z=339.1.

Method F

To a solution of 0.066 g (0.2 mmol) of compound 1 in 2 mL of concentrated sulfuric acid was added 0.2 mL of concentrated nitric acid at 0° C. The mixture was stirred at room temperature for 1 hour, and poured into 20 mL of ice-water. It was basified with sodium carbonate, and extracted with two 30 mL portions of methylene chloride. The combined organic extracts were washed with 20 mL of brine, and concentrated. The residue was purified by preparative TLC eluting with 4% methanol in methylene chloride to give 0.021 g of compound 7. Calculated MS for $C_{17}H_{20}N_5O_3S=374.1$. found m/z=374.1.

Method G

To a suspension of 0.06 g (0.17 mmol) of compound 8 in 1 mL of formic acid were added 0.28 g (5 mmol) of iron powder and 2 mL of 6N HCl. The mixture was stirred at reflux for 3 hours and quenched with 60 mL of saturated sodium bicarbonate. It was extracted with three 50 mL portions of methylene chloride. The combined organic extracts were washed with 40 mL of brine, and concentrated. The residue was purified by preparative TLC eluting with 8% methanol in methylene chloride to give 0.021 g of compound 9. Calculated MS for $C_{17}H_{18}N_5OS=340.1$. found m/z=340.1.

Method H

A mixture of 0.3 g (0.8 mmol) of compound 7 and 1 mL of 28% ammonium hydroxide in 8 mL of acetonitrile in a sealed tube was heated at 100° C. for 2 hours and cooled to room temperature. It was diluted with 5 mL of methanol and filtered to give 0.24 g of compound 10. Calculated MS for $C_{15}H_{16}N_5O_3S=346.1$. found m/z=346.1.

Method I

A mixture of 0.17 g (0.5 mmol) of compound 10 and 0.03 g of 10% Pd/C in 25 mL of methanol was stirred under hydrogen atmosphere (balloon) at room temperature for 90 hours. It was diluted with 150 mL of methanol, filtered and concentrated to give 0.14 g of compound 11. Calculated MS for $C_{15}H_{18}N_5OS=316.1$. found m/z=316.1

Method J

A mixture of 0.048 g (0.15 mmol) of compound 11 in 3 mL of HCOOH—HCl(Conc.)-$H_2O$ (1:1:1) was heated at reflux for 18 hours and concentrated. The residue was stirred in 1 mL of HCOOH and 10 mL of o-xylene for additional 24 hours, concentrated. The residue was purified by preparative TLC eluting with 7% methanol in methylene chloride to give 0.016 g of compound 12. Calculated MS for $C_{16}H_{16}N_5OS=326.1$. found m/z=326.2.

Method K

To a stirred solution of 0.048 g (0.15 mmol) of compound 11 in 2 mL concentrated hydrochloric acid was added a solution of 0.014 g (0.2 mmol) of sodium nitrite in 1 mL of water at room temperature slowly. After 1 hour it was quenched with 50 mL of saturated sodium bicarbonate and extracted with two 50 mL portions of methylene chloride to remove impurities. The solid was collected by filtration, washed with water and methylene chloride, and dried to give 0.038 g of compound 13. Calculated MS for $C_{15}H_{15}N_6OS=327.1$. found m/z=327.2.

Method L

To a stirred solution of 18.5 g (57.2 mmol) of compound 14b in 525 mL of methylene chloride was added 16.2 mL (172 mmol) of boron tribromide at −78° C. The reaction was warmed to room temperature over 2 hour and stirred for additional 20 hours. It was cooled to −78° C., quenched with 50 mL of methanol and heated at reflux for 1 hour. The mixture was concentrated; the residue was stirred with 200 mL of saturated sodium bicarbonate and filtered to give 15.1 g of compound 15b. Calculated MS for $C_{16}H_{12}N_3O_2S=310.1$. found m/z=310.1.

Compound 15a was prepared from compound 14a analogously. Calculated MS for $C_{15}H_9ClN_3O_2S=330.0$. found m/z=330.2.

Method M

To a stirred suspension of 5.0 g (16.2 mmol) of compound 15b in 50 mL of acetic acid was added 17.8 (1M, 17.8 ol) of bromine in acetic acid at room temperature. The mixture was stirred for 6 hours and concentrated to give 7.07 g of product 16b as acetate salt. Calculated MS for $C_{16}H_{11}BrN_3O_2S=390.0$. found m/z=389.9.

Compound 16a was prepared from compound 15a analogously. Calculated MS for $C_{15}H_8BrClN_3O_2S=407.9$. found m/z=407.9.

Method N

A mixture of 7.07 g (15.8 mmol) of compound 16b and 100 mL of $POCl_3$ was heated at reflux for 4 hours and the excess POCl$_3$ was evaporated under vacuum. The residue was diluted with saturated NaHCO$_3$ and extracted with 900 mL of methylene chloride. The combined organic extracts were concentrated and the residue was chromatographed eluting with 5% acetone in methylene chloride to give 5.05 g of compound 17b. Calculated MS for C$_{16}$H$_{11}$BrClN$_3$OS=408.0. found m/z=408.0.

Compound 17a was prepared from compound 16a analogously. Calculated MS for C$_{15}$H$_7$BrCl$_2$N$_3$OS=333.1. found m/z=333.2.

Method O

A mixture of 0.43 g (1 mmol) of compound 17a, 0.38 g (1.2 mmol) of vinyltributyltin, 0.10 g (cat.) of Pd (PPh$_3$)$_4$ and 0.2 g (1.5 mmol) of diisopropylethylamine in 14 mL of toluene-trifluoromethylbenzene (1:1) and 1 mL of DMF in a sealed tube was heated at 140° C. for 40 minutes using microwave irradiation (Personalchemistry). The same reaction was run for another three times. The combined reaction mixtures were concentrated. The residue was purified by chromatography eluting with 1 to 4% acetone in methylene chloride to give 0.52 g of compound 18a. Calculated MS for C$_{17}$H$_{10}$Cl$_2$N$_3$OS=374.0. found m/z=374.2.

Compound 18b was prepared from compound 17b analogously. Calculated MS for C$_{18}$H$_{13}$ClN$_3$OS=354.1. found m/z=354.1.

Method P

To a suspension of 0.24 g (0.64 mmol) of compound 18a in 70 mL of THF-H$_2$O (7:3) were added 1.3 g (6.1 mmol) of sodium periodate and 1 mL of Osmium tetraoxide in tert-Butanol (2.5% wt). The mixture was stirred at room temperature for three days. It was quenched with 30 mL of 25% Na$_2$S$_2$O$_3$, extracted with three 70 mL portions of methylene chloride. The combined organic extracts were washed with 30 mL of brine and concentrated. The residue was purified by chromatography eluting with 1 to 4% acetone in methylene chloride to give 0.165 g of compound 19a. Calculated MS for C$_{16}$H$_8$Cl$_2$N$_3$O$_2$S=376.0. found m/z=376.2.

Compound 19b was prepared from compound 18b analogously. Calculated MS for C$_{17}$H$_{11}$ClN$_3$O$_2$S=356.0. found m/z=356.0.

Method Q

A mixture of 0.04 g (0.1 mmol) of compound 19a and 0.1 g (excess) of hydrazine monohydrate in 15 mL of tert-butanol was stirred at 70° C. for 3 hours. The precipitate was collected by filtration and then purified by reverse phase HPLC(C-18 BHK column, 95-5% water/5-95% MeCN/0.1% HCOOH) to give 0.008 g of compound 20a. Calculated MS for C$_{16}$H$_9$ClN$_5$OS=354. found m/z=354.2.

Compound 20b was prepared from compound 19b analogously. Calculated MS for C$_{17}$H$_{12}$N$_5$OS=334.1. found m/z=334.2.

Method R

A solution of 0.095 g (0.24 mmol) of compound 21 in 1 mL of 1M HCl and 8 mL of THF was stirred at reflux for 16 hours and concentrated. The residue was partitioned between 20 mL of methylene chloride and 10 mL of saturated sodium bicarbonate. The aqueous layer was extracted with two 10 mL portions of methylene chloride. The combined organic extracts were washed with 40 mL of brine, concentrated to give 0.086 g of compound 22 as a solid. Calculated MS for C$_{18}$H$_{13}$ClN$_3$O$_2$S=370.0. found m/z=370.0.

Method S

To a stirred solution of 0.07 g (0.19 mmol) of compound 22 in 28 mL of methanol was added 0.007 g (0.19 mmol) of sodium borohydride in portions. After 25 minutes, it was quenched with 2 mL of water and concentrated. The residue was partitioned between 40 mL of methylene chloride and 20 mL of water. The aqueous layer was extracted with 30 mL of methylene chloride. The combined organic extracts were concentrated; the residue was purified by preparative TLC eluting with 5% acetone in methylene chloride to give 0.023 g of compound 23. Calculated MS for C$_{18}$H$_{15}$ClN$_3$O$_2$S=372.1. found m/z=372.0.

Method T

A suspension of 0.023 g (0.062 mmol) of compound 23 and 0.003 g (0.124 mmol) of 60% NaH in oil in 2.5 mL of THF was stirred at reflux for 2 hours, cooled to room temperature, and quenched with 1 mL of water. It was concentrated and the residue was partitioned between 10 mL of methylene chloride and 5 mL of water. The aqueous layer was extracted with two 20 mL portions of methylene chloride. The combined organic extracts were concentrated; the residue was purified by preparative TLC eluting with 15% acetone in methylene chloride to give 0.010 g of compound 24. Calculated MS for C$_{18}$H$_{14}$N$_3$O$_2$S=336.1. found m/z=336.1.

Method U

To a stirred suspension of 1.32 g (4.1 mmol) of compound 25b in 60 mL of acetic acid was added 5 mL (1M, 5 mmol) of bromine in acetic acid at room temperature. The mixture was stirred for 20 minutes and concentrated. The residue was stirred with 80 mL of methanol and filtered to give 1.28 g of compound 26b. Calculated MS for C$_{16}$H$_{12}$BrN$_4$O$_2$S=405.0. found m/z=405.2.

Compound 26a was prepared from compound 25a analogously. Calculated MS for C$_{16}$H$_{12}$BrN$_4$OS=387.0. found m/z=387.1.

Method V

A mixture of 0.60 g (1.5 mmol) of compound 26b, 1.1 g (3 mmol) of ethoxyvinyltributyltin, 0.10 g (cat.) of Pd(PPh$_3$)$_4$ and 0.645 g (5.0 mmol) of diisopropylethylamine in 12 mL of toluene-trifluoromethylbenzene (1:1) in a sealed tube was heated at 180° C. for 3 hour using microwave irradiation (Personalchemistry). It was concentrated; the residue in 1 mL of hydrochloric acid (1M) and 8 mL of THF was stirred at reflux for 3 hours and concentrated. The residue was purified by chromatography eluting with 1 to 4% methanol in methylene chloride to give 0.13 g of compound 27b. Calculated MS for C$_{18}$H$_{13}$N$_4$O$_2$S=349.1. found m/z=349.2.

Compound 27a was prepared from compound 26a analogously. Calculated MS for C$_{18}$H$_{13}$N$_4$OS=333.1. found m/z=333.2.

Method W

A suspension of 0.23 g (0.6 mmol) of compound 25a and 0.19 g (1.2 mmol) of potassium xanthate in 4 mL of DMF in a sealed tube was stirred at 160° C. for 7 hours and the solvent was evaporated under vacuum. The residue was stirred with 40 mL of methylene chloride-methanol (1:1) and filtered to give 0.17 g of compound 28 as a pale yellow solid. Calculated MS for C$_{17}$H$_{11}$N$_4$OS$_3$=383.0. found m/z=383.1.

Method X

To a stirred solution of 0.035 g (0.09 mmol) of compound 28 in 3 mL of DMF was added 0.028 g (0.2 mmol) of potassium carbonate. After 30 minutes, a solution of 0.017 g (0.12 mmol) of iodomethane in 1 mL of DMF was added and the mixture was stirred at room temperature for additional 30 minutes. It was concentrated and the residue was taken up in 50 mL of methylene chloride and 30 mL of water. The aqueous layer was extracted with 20 mL of methylene chloride.

The combined organic extracts were washed with 20 mL of brine and concentrated. The residue was purified by chromatography eluting with 1 to 4% methanol in methylene chloride plus 1% ammonium hydroxide to give 0.027 g of compound 29. Calculated MS for $C_{18}H_{13}N_4OS_3$=397.0. found m/z=397.1.

Method Y

To a stirred suspension of 0.105 g (0.27 mmol) of compound 29 in 5 mL of DMF was added 0.72 g (1.3 mmol) of sodium methoxide. The mixture was stirred at room temperature for 18 hours and quenched with one drop of water, and concentrated. The residue was purified by chromatography eluting with 1 to 5% methanol in methylene chloride plus 1% ammonium hydroxide to give 0.048 g of compound 30. Calculated MS for $C_{17}H_{11}N_4O_2S_2$=367.0. found m/z=367.1.

Method Z:

To a solution of 0.08 g (0.24 mmol) of compound 27a in 8 mL of DMF were added 0.14 g (1 mmol) of potassium carbonate and 0.1 g (excess) of iodomethane. The mixture was stirred at room temperature for 18 h, and concentrated. The residue was purified by chromatography eluting with 1% to 5% methanol in methylene chloride plus 1% ammonium hydroxide to give a crude product, which was further purified by preparative TLC eluting with methanol in methylene chloride to give 0.026 g of compound 31. MS Calcd for $C_{19}H_{15}N_4OS$ m/z=347.1. found m/z=347.2.

Method M

A mixture of 0.3 g (0.74 mmol) of compound 26c, 0.4 g (1.2 mmol) of allyltributyltin, and 0.26 g (2 mmol) of diisopropylethylamine, and 0.08 g of Pd(PPh$_3$)$_4$ in 4 mL of toluene and 1 mL of trifluoromethylbenzene in a sealed tube was heated at 175° C. for 30 min (in microwave, personalChemistry). It was concentrated, the residue was purified by chromatography eluting with 4% methanol in methylene chloride to give 0.1 g of compound 32. MS Calcd for $C_{18}H_{14}ClN_4OS$ m/z=369.1. found m/z=369.2.

Method AB

To a stirred suspension of 0.12 g (0.33 mmol) of compound 32 in 30 mL of THF-H$_2$O (1:1) were added 0.3 mL of OsO$_4$ (2.5% wt in t-BuOH) and 0.077 g (0.66 mmol) of NMO. The mixture was stirred at room temperature for 2 days, and quenched with 5 mL of sodium thiosulfite. It was concentrated, the residue was stirred with 200 mL of methylene chloride-methanol (1:1) and then filtered. The filtrate was concentrated; the residue was purified by preparative TLC eluting with 8% methanol in methylene chloride to give 0.038 g of compound 33. MS Calcd for $C_{18}H_{16}ClN_4O_3S$ m/z=403. found m/z=403.2.

Method AC

A mixture of 0.037 g (0.1 mmol) of compound 33, 0.04 g (0.2 mmol) of sodium periodate in 30 mL of H$_2$O was stirred at room temperature for 90 h and concentrated. The residue was purified by chromatography eluting with 1% to 5% methanol in methylene chloride plus 1% ammonium hydroxide to give 0.028 g of compound 34. MS Calcd for $C_{17}H_{10}ClN_4OS$ m/z=353.0. found m/z=353.2.

Method AD

A mixture of 0.19 g (0.44 mmol) of compound 17a, 0.1 g (excess) of hydroxyethylamine in 10 mL of MeCN was stirred at 100° C. for 1 day and cooled to room temperature. The reaction was filtered and washed with 4 mL of methanol to give 0.16 g of compound 37a. MS Calcd for $C_{17}H_{13}BrClN_4O_2S$ m/z=453.0. found m/z=453.2.

The following compounds were prepared analogously:

| Compound No. | Compound | Molecular Formula | MW | MS Observed |
|---|---|---|---|---|
| 37a | 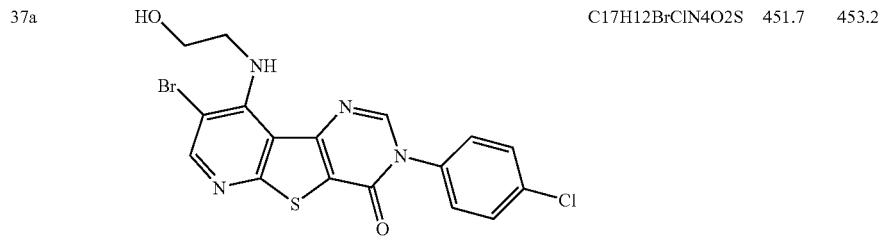 | C17H12BrClN4O2S | 451.7 | 453.2 |
| 37b | 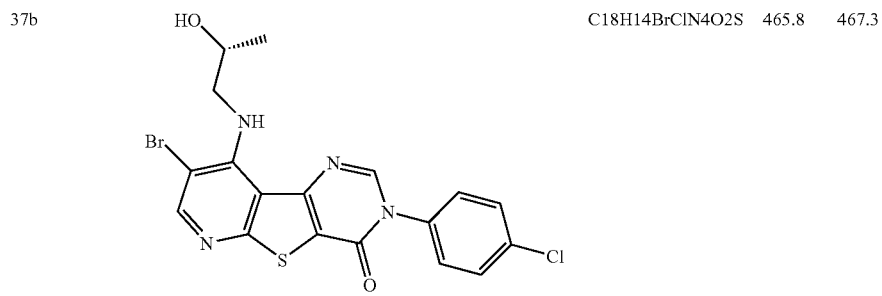 | C18H14BrClN4O2S | 465.8 | 467.3 |

-continued

| Compound No. | Compound | Molecular Formula | MW | MS Observed |
|---|---|---|---|---|
| 37c | | C18H14BrClN4O2S | 465.8 | 467.3 |
| 37d | | C18H14BrClN4O2S | 465.8 | 467.3 |
| 37e | | C18H14BrClN4O2S | 465.8 | 467.3 |
| 37f | | C19H17BrN4O2S | 445.3 | 446.9 |

Method AE

A mixture of 0.12 g (0.27 mmol) of compound 37, 0.1 g (0.44 mmol) of Pd(OAc)$_2$, and 0.2 g (0.5 mmol) of racemic-2-(di-t-butylphosphino)-1,1'-binaphthyl, and 0.18 g (0.55 mmol) of Cs$_2$CO$_3$ in 7 mL of toluene in a sealed tube was heated at 125° C. for 20 h. It was concentrated; the residue was purified by chromatography eluting with 1% to 5% methanol in methylene chloride plus 1% ammonium hydroxide to give 0.037 g of compound 38a. MS Calcd for C$_{17}$H$_{11}$ClN$_4$O$_2$S m/z=371.1. found m/z=371.2.

The following compounds were prepared analogously:

| Compound No. | Compound | Molecular Formula | MW | MS Observed |
|---|---|---|---|---|
| 38a | | C17H11ClN4O2S | 370.8 | 371.2 |
| 38b | | C18H13ClN4O2S | 384.8 | 385.2 |
| 38c | | C18H13ClN4O2S | 384.8 | 385.2 |
| 38d | | C18H13ClN4O2S | 384.8 | 385.2 |
| 38e | | C18H13ClN4O2S | 384.8 | 385.2 |
| 38f | | C19H16N4O2S | 364.4 | 365.2 |
| 38g | | C19H16N4O2S | 364.4 | 365.2 |
| 38h | | C18H14N4O2S | 350.4 | 351.2 |

| Compound No. | Compound | Molecular Formula | MW | MS Observed |
|---|---|---|---|---|
| 38i | | C18H14N4O3S | 366.4 | 367.2 |

Method AF

A mixture of 0.25 g (0.7 mmol) of compound 39 and 1.2 mL of nitric acid in 15 mL of TFA was stirred at reflux for 1 h, then cooled to room temperature and concentrated. The residue was purified by preparative TLC eluting with 5% methanol in dichloromethane containing 1% NH$_4$OH and to give 0.15 g of compound 40a MS Calcd for $C_{15}H_9ClN_5O_3S$ m/z=374.0. found m/z=374.2. and 0.08 g of compound 40b. MS Calcd for $C_{16}H_{11}ClN_5O_3S$ m/z=388.0. found m/z=388.2.

Method AG

A mixture of 0.14 g (~0.38 mmol) of compound 40a and 0.25 g of tin chloride in 5 mL of concentrated HCl was stirred at reflux for 18 h, then concentrated. To this residue were added 1 mL of HCOOH, 0.02 g of p-toluenesulfonic acid and 10 mL of oxylene. The mixture was stirred at reflux for 2 days, concentrated. The residue was purified by chromatography eluting with 1% to 5% methanol in methylene chloride plus 1% ammonium hydroxide to give 0.012 g of compound 35. MS Calcd for $C_{16}H_9ClN_5OS$ m/z=354.0. found m/z=354.2.

The following compounds were prepared analogously from 40a and 40b respectively:

IC$_{50}$ Determination

A CHO cell line stably expressing hmGluR1 receptor was established. One day prior to assay, cells were split in growth media at concentration of 50,000 cells/well in a volume of 100 µl and seeded into black clear-bottom 96-well plates. After two to six hours, when cells were well attached to the plate, growth medium was replaced with assay medium (100 µL) consisting of DMEM high glucose, supplemented with GPT (1 U/mL) and sodium pyruvate, 1 mM. Following overnight incubation, medium was discarded and cells were loaded for 2 hours with dye from the Calcium 3 Assay Reagent Kit (Molecular Devices, # R8033), prepared according to manufacturers' instructions. A 96-tip pipettor/fluorometric imaging plate reader (FLIPR 384; Molecular Devices) was used and intracellular calcium mobilization was measured by increases in fluorescence upon agonist Quisqualate stimulation following 6 sec-baseline measurement. Test compounds were added 10 minutes before Quisqualate. IC$_{50}$ determinations for tested compounds were generated against Quisqualate 1 µM corresponding to EC$_{80}$ value in a standard dose response curve.

In the table below, those compounds having an mGluR1 IC$_{50}$ value of less than 20 nM (<20 nM) are designated with letter "A"; those with an IC$_{50}$ value of from 20 to less than 100 nM (10–<100 nM) are designated with letter "B"; those with an IC$_{50}$ value of from 100 to 1000 nM are designated with letter "C"; and those with an IC$_{50}$ value of more than 1000 nM (>1000 nM) are designated with letter "D".

| Compound No. | Compound | Molecular Formula | MW | MS Observed |
|---|---|---|---|---|
| 35 | | C16H8ClN5OS | 353.8 | 354.2 |
| 36 | | C17H10ClN5OS | 367.8 | 368.2 |

TABLE 2

| No | Structure | mGluR1 IC$_{50}$ rating |
|---|---|---|
| 4 | 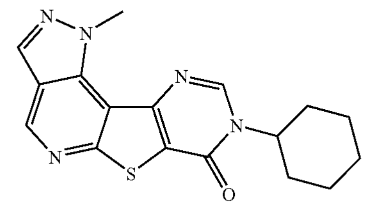 | C |
| 6 | 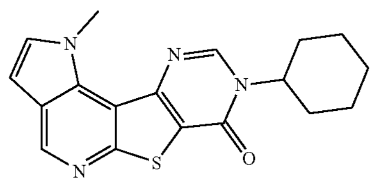 | B |
| 9 | 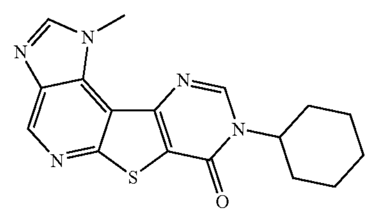 | B |
| 12 | 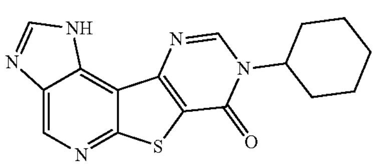 | B |
| 13 | 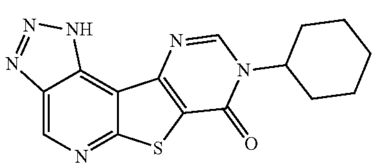 | C |
| 20a | 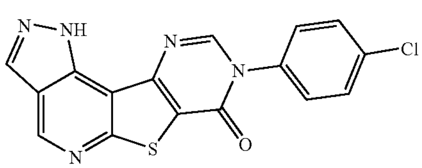 | B |
| 20b | 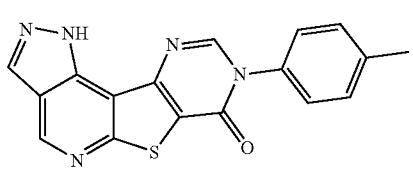 | A |
| 24 | 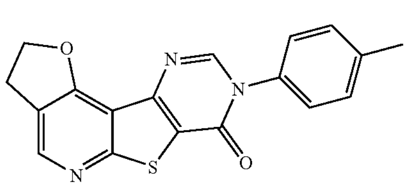 | C |

TABLE 2-continued

| No | Structure | mGluR1 IC$_{50}$ rating |
|---|---|---|
| 27a | 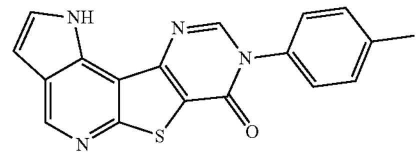 | A |
| 27b | 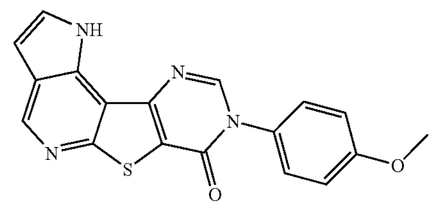 | A |
| 28 | 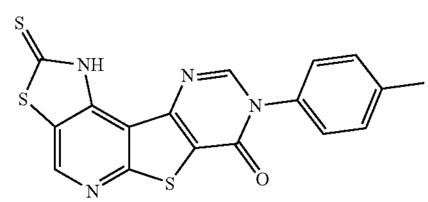 | C |
| 29 | 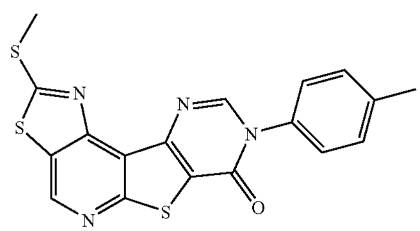 | C |
| 30 | 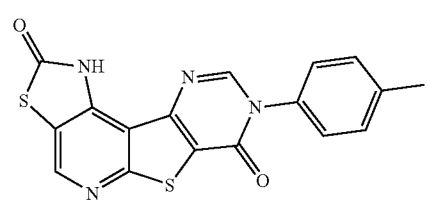 | C |
| 31 | 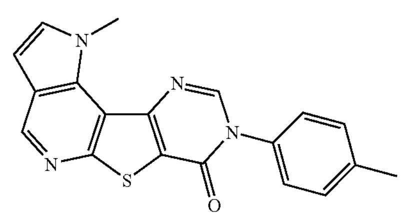 | B |
| 34 | 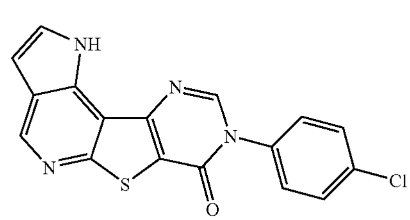 | A |

TABLE 2-continued

| No | Structure | mGluR1 IC$_{50}$ rating |
|---|---|---|
| 35 | 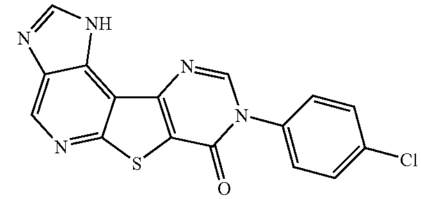 | A |
| 36 | 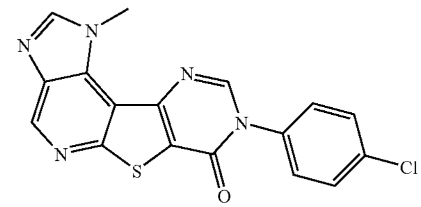 | A |
| 37a | 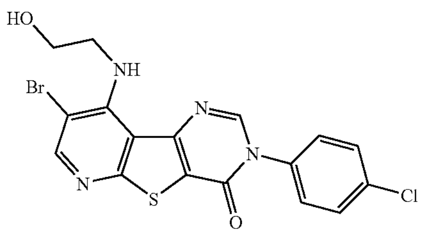 | A |
| 37b | 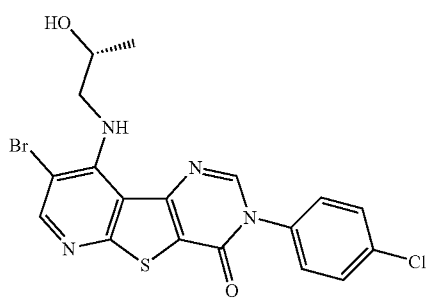 | D |
| 37c | 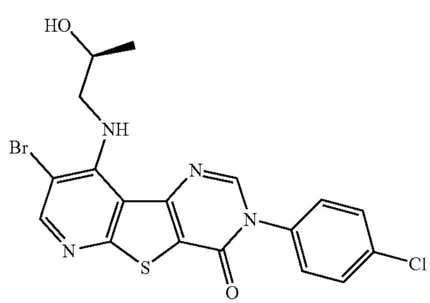 | D |
| 37d | 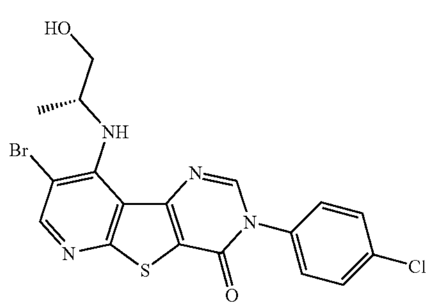 | D |
| 37e | | D |
| 37f | | C |
| 38a | | A |
| 38b | | A |
| 38c | | A |
| 38d | | B |

TABLE 2-continued

| No | Structure | mGluR1 IC$_{50}$ rating |
|---|---|---|
| 38e | 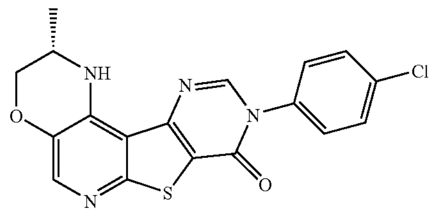 | A |
| 38f | 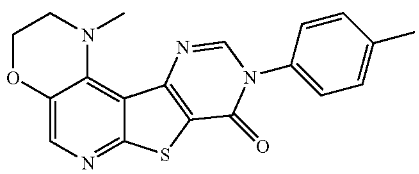 | A |
| 38g | 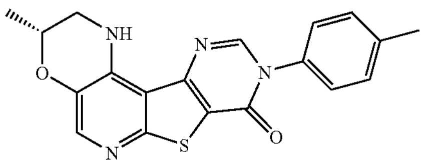 | A |
| 38h | 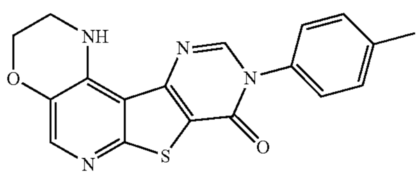 | A |
| 38i | 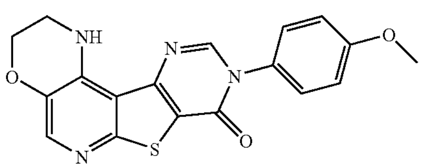 | A |

Specific IC$_{50}$ values for representative compounds are shown in Table 3 below.

TABLE 3

| No | Structure | mGluR1 IC$_{50}$ (nM) |
|---|---|---|
| 27a | 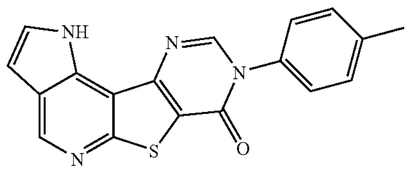 | 0.7 |
| 27b | 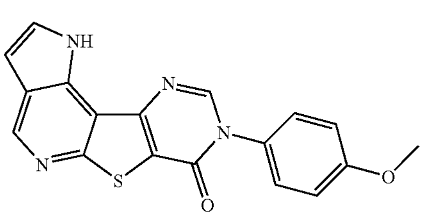 | 4.9 |

TABLE 3-continued

| No | Structure | mGluR1 IC$_{50}$ (nM) |
|---|---|---|
| 20b | 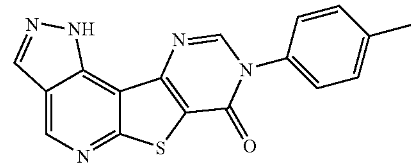 | 17 |
| 12 | 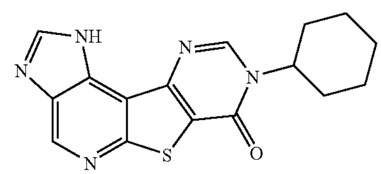 | 23 |
| 20a | 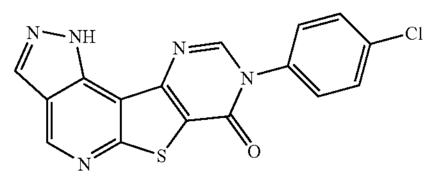 | 38 |
| 34 | 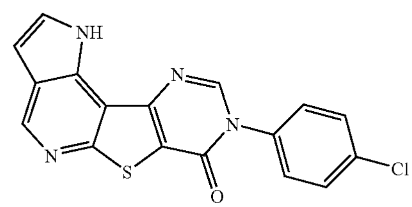 | 0.4 |
| 35 | 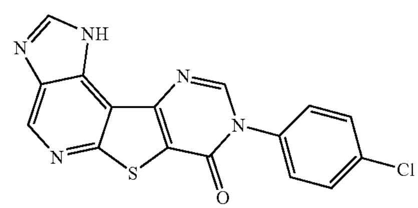 | 6.0 |
| 36 | 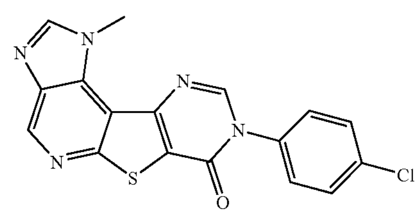 | 9.8 |
| 37a | 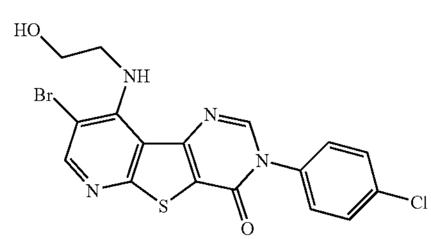 | 14.2 |

TABLE 3-continued

| No | Structure | mGluR1 IC$_{50}$ (nM) |
|---|---|---|
| 38a | 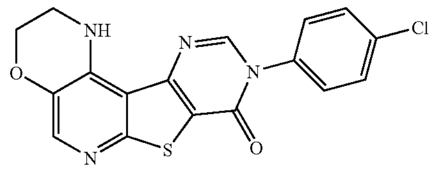 | 2.9 |
| 38b | 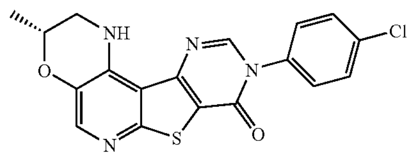 | 1.4 |
| 38c | 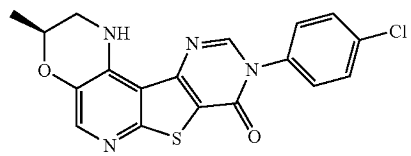 | 2.2 |
| 38e | 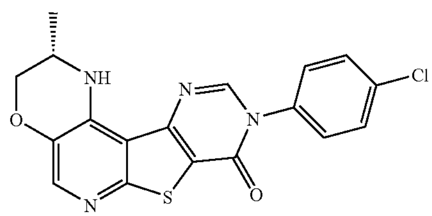 | 12 |
| 38f | 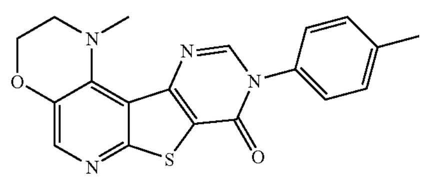 | 5.7 |
| 38g | 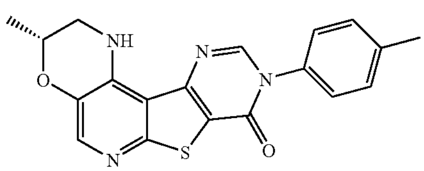 | 5.3 |
| 38h | 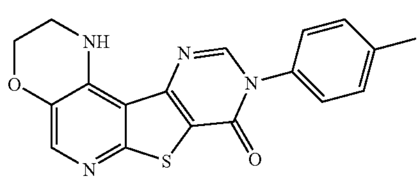 | 2.2 |
| 38i | 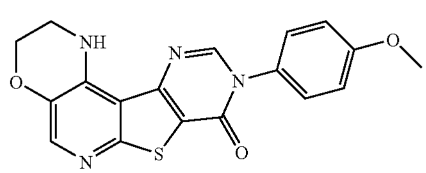 | 2.5 |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A compound of formula I:

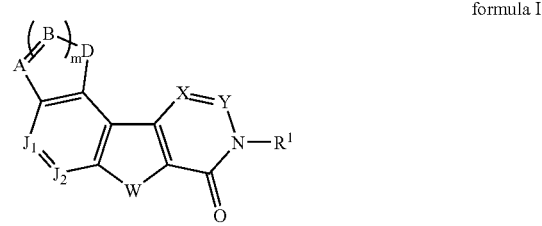

formula I or a pharmaceutically acceptable salt thereof, wherein:
W is S;
X is N;
Y is CR$^2$;
J$_1$ is C(R$^4$);
J$_2$ is N;
R$^1$ is selected from the group consisting of —H, —NR$^5$R$^6$, —OR$^5$, —SR$^9$, —CN, —C(O)R$^6$, —C(O$_2$)R$^6$, —OC(O)R$^6$, —C(O)NR$^6$R$^7$, —N(R$^6$)C(O)R$^7$, —S(O$_2$)NR$^6$R$^7$—N(R$^6$)S(O$_2$)R$^9$, —N(R$^6$)C(O)NR$^6$R$^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^8$;
R$^2$ and R$^3$ are each independently selected from the group consisting of H, halo, —CN, —NO$_2$, —OR$^5$, —SR$^9$, —NR$^5$R$^6$, —C(O)R$^6$, —C(O$_2$)R$^6$, —OC(O)R$^6$, —C(O)NR$^6$R$^7$, —N(R$^6$)C(O)R$^7$, —OS(O$_2$)R$^9$, —S(O$_2$)R$^9$, —S(O$_2$)NR$^6$R$^7$, —N(R$^6$)S(O$_2$)R$^9$, and —N(R$^6$)C(O)NR$^6$R$^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^8$;
R$^4$ is independently selected from the group consisting of H, halo, —CN, —NHC(O)R$^6$, —NHSO$_2$R$^9$, —NR$^5$R$^6$, —OR$^5$, —C(O)R$^6$, —C(O$_2$)R$^6$, —C(O)NR$^6$R$^7$; and alkyl, alkoxy, alkenyl, alkynyl, cycloalkyl, cycloalkoxy, aryl, aryloxy, arylalkyl, heteroaryl, heteroarylalkyl, heterocyclyl; and heterocyclylalkyl groups optionally substituted with at least one R$^8$;
R$^5$ is selected from the group consisting of H, —C(O)OR$^6$, —SO$_2$R$^9$, —C(O)NR$^6$R$^7$, and alkyl, cycloalkyl, aryl, arylalkyl, heteroaryl, heteroarylalkyl, heterocyclyl, and heterocyclylalkyl groups optionally substituted with at least one R$^8$;
R$^6$ and R$^7$ are independently selected from the group consisting of H and alkyl, cycloalkyl, aryl, arylalkyl, heteroaryl, heteroarylalkyl, heterocyclyl, and heterocyclylalkyl groups optionally substituted with at least one R$^8$; or
R$^5$ and R$^6$ or R$^6$ and R$^7$, when attached to the same nitrogen atom, optionally taken together with the nitrogen atom form a 3-8 membered heterocyclic ring containing 0-3 heteroatoms independently selected from O, N or S in addition to said nitrogen atom;
R$^8$ is selected from the group consisting of H, halo, —OR$^5$, —NO$_2$, —CN, —NR$^6$C(O)R$^7$, —NR$^6$SO$_2$R$^9$, —NR$^5$R$^6$, —C(O)R$^6$, —C(O)R$^6$, —C(O)NR$^6$R$^7$, —S(O$_2$)NR$^6$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one of halo, —CN, —NO$_2$, —OR$^5$, —SR$^9$, —NR$^6$R$^7$, —C(O)R$^6$, —OC(O$_2$)R$^6$, —OC(O)R$^6$, —C(O)NR$^6$R$^7$, —N(R$^6$)C(O)R$^7$, —OS(O$_2$)R$^9$, —S(O$_2$)R$^9$, —S(O$_2$)NR$^6$R$^7$, —N(R$^6$)C(O)NR$^6$R$^7$, and —NR$^6$SO$_2$R$^9$;

R$^9$ is selected from the group consisting of alkyl, cycloalkyl, aryl, arylalkyl, heteroaryl, heteroarylalkyl, heterocyclyl, and heterocyclylalkyl groups optionally substituted with at least one R$^8$;

R$^{10}$ is selected from the group consisting of H, —C(O)R$^6$, —C(O)OR$^6$, —SO$_2$R$^9$, —C(O)NR$^6$R$^7$, and alkyl, cycloalkyl, aryl, arylalkyl, heteroaryl, heteroarylalkyl, heterocyclyl, and heterocyclylalkyl groups optionally substituted with at least one R$^8$, A is selected from the group consisting of CHR$^4$, CR$^4$, O, S, N, NR$^4$, C=O, and C=S;

B is selected from the group consisting of N, NR$^4$, CHR$^4$, CR$^4$, O, S, C=O, C=S, and C—S—R$^9$;

D is selected from the group consisting of CHR$^4$, O, S, and NR$^4$; and m is 1-3.

2. The compound of claim 1, wherein

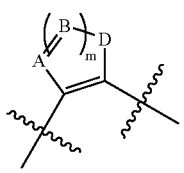

is selected from the group consisting of:

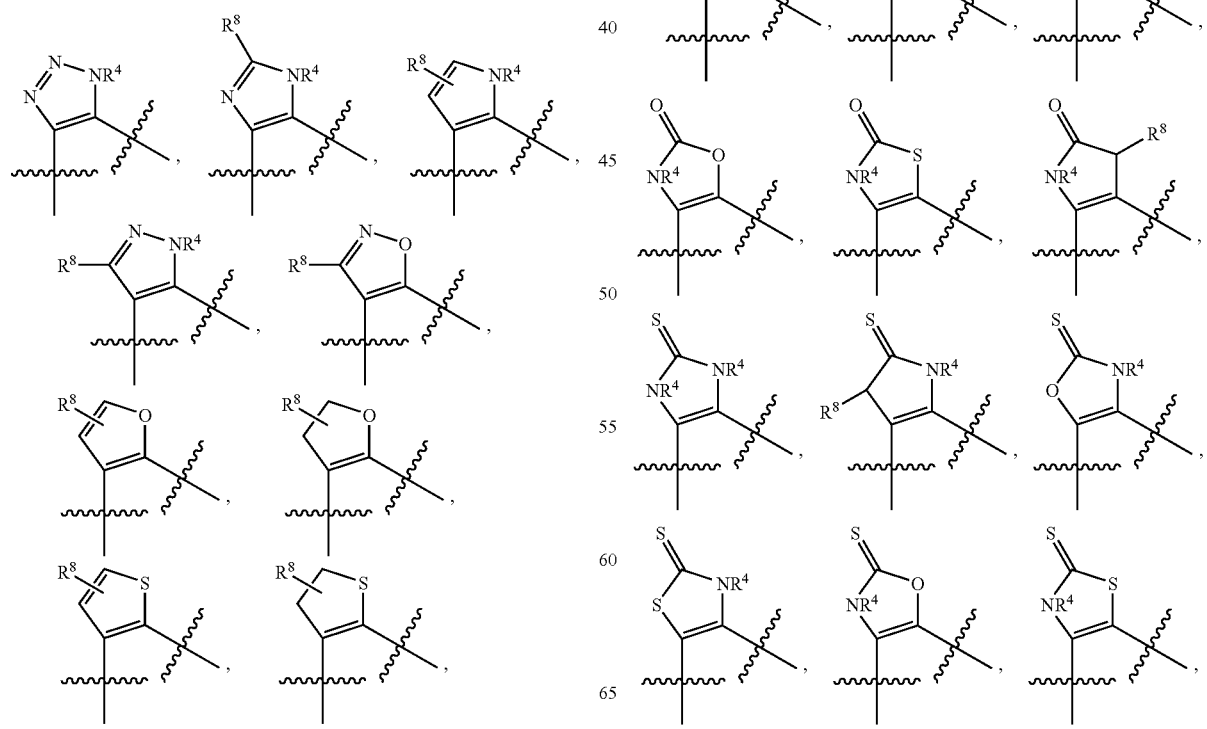

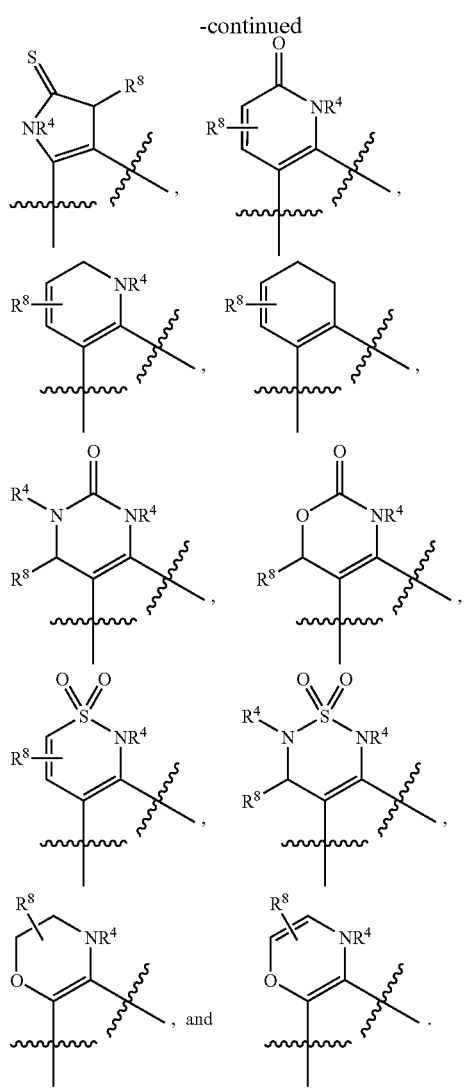

3. The compound of claim 1, wherein A and B are selected from the group consisting of $CHR^4$ and $CR^4$, and D is $NR^4$.

4. The compound of claim 1, wherein A is $CHR^4$ or $CR^4$, B is N or $NR^4$; and D is $NR^4$.

5. The compound of claim 1, wherein A is N or $NR^4$, D is $NR^4$, and B is $CHR^4$ or $CR^4$.

6. The compound of claim 1, wherein A and B are selected from the group consisting of $CHR^4$ and $CR^4$, and D is O.

7. The compound of claim 1, wherein A and B are selected from the group consisting of $CHR^4$ and $CR^4$, and D is S.

8. The compound of claim 1, wherein A and B are selected from the group consisting of $CHR^4$ and $CR^4$ and D is $CR^4$.

9. The compound of claim 1, wherein A is N or $NR^4$, B is $CHR^4$ or $CR^4$, and D is $NR^4$.

10. The compound of claim 1, wherein A is O, B is $CHR^4$ or $CR^4$, and D is $NR^4$.

11. The compound of claim 1, wherein A is S, B is selected from the group consisting of C=O, C=S, and C—S—$R^9$, and D is $NR^4$.

12. The compound of claim 1 wherein W is S and $R^1$ is cyclohexyl.

13. The compound of claim 1, wherein W is S and $R^1$ is p-methylphenyl.

14. The compound of claim 1, wherein W is S and $R^1$ is p-methoxyphenyl.

15. The compound of claim 1, wherein W is S and $R^1$ is p-halophenyl.

16. The compound of claim 1, wherein the compound is selected from the group consisting of those set forth below or a pharmaceutically acceptable salt thereof:

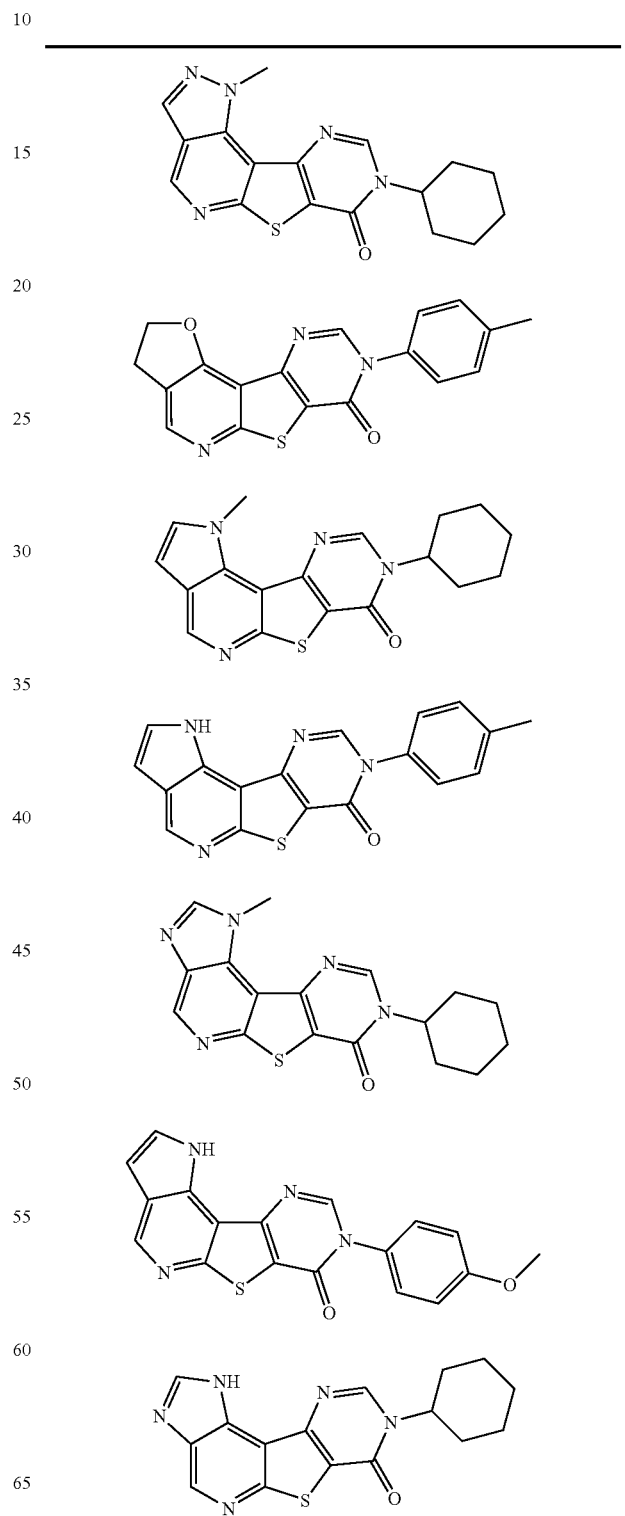

-continued
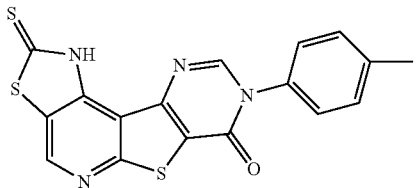
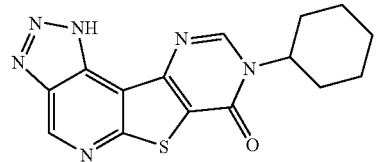
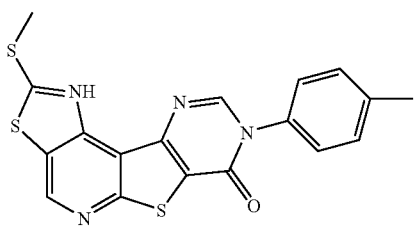
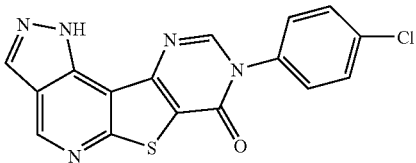
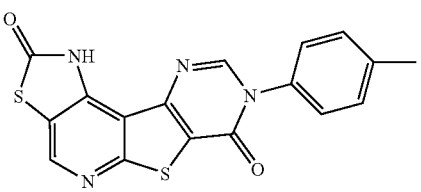
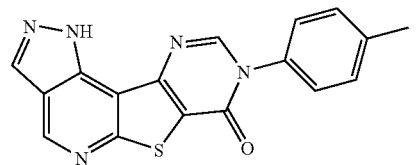
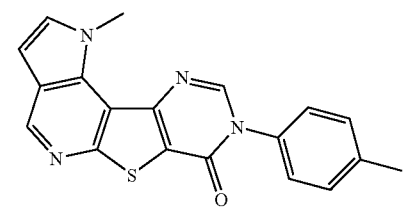
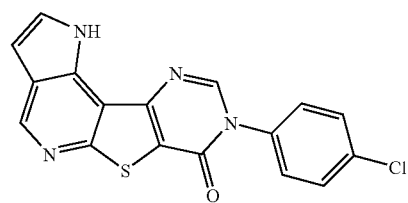
-continued
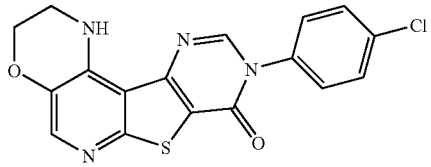
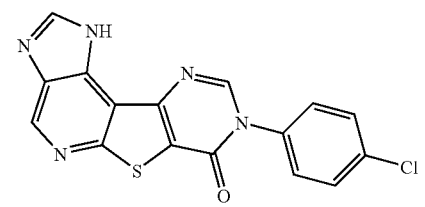
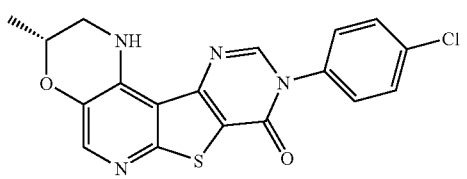
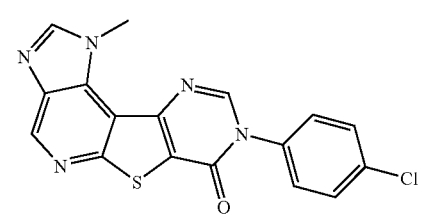
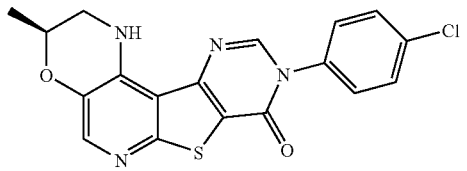
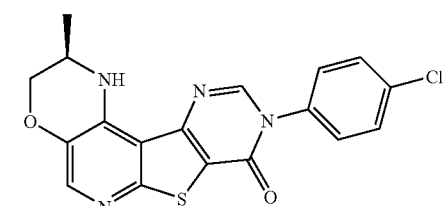
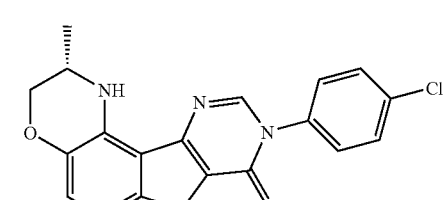
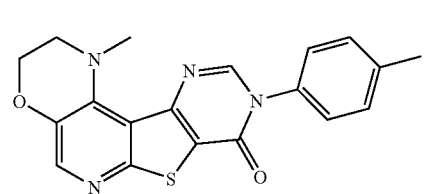

-continued

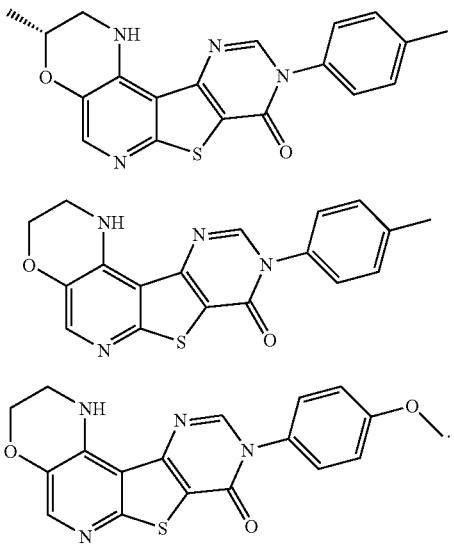

17. A pharmaceutical composition comprising at least one compound of claim 1, or a pharmaceutically acceptable salt thereof and at least one pharmaceutically acceptable carrier, adjuvant or vehicle.

18. A pharmaceutical composition comprising at least one compound of claim 16, or a pharmaceutically acceptable salt thereof and at least one pharmaceutically acceptable carrier, adjuvant or vehicle.

19. The pharmaceutical composition of claim 17, further comprising one or more additional therapeutic agents.

20. The pharmaceutical composition of claim 18, further comprising one or more additional therapeutic agents.

21. The pharmaceutical composition of claim 19, wherein said additional therapeutic agents are selected from the group consisting of therapeutic agents suitable for pain management, anti-anxiety agents, anti-migraine agents, and therapeutic agents suitable for treating urinary incontinence.

22. The pharmaceutical composition of claim 20, wherein said additional therapeutic agents are selected from the group consisting of therapeutic agents suitable for pain management, anti-anxiety agents, anti-migraine agents, and therapeutic agents suitable for treating urinary incontinence.

23. A compound of claim 1, in isolated and purified form.

\* \* \* \* \*